(12) United States Patent
Carlstrom et al.

(10) Patent No.: US 10,471,241 B2
(45) Date of Patent: Nov. 12, 2019

(54) SHEATHLESS GUIDE, RAPID EXCHANGE DILATOR AND ASSOCIATED METHODS

(71) Applicant: Merit Medical Systems, Inc., South Jordan, UT (US)

(72) Inventors: Steve W. Carlstrom, Salt Lake City, UT (US); Jim Mottola, Salt Lake City, UT (US); Punit Satyavrat Ramrakha, South Jordan, UT (US); Nate Shirley, Herriman, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 852 days.

(21) Appl. No.: 14/467,830

(22) Filed: Aug. 25, 2014

(65) Prior Publication Data

US 2015/0057697 A1 Feb. 26, 2015

Related U.S. Application Data

(60) Provisional application No. 61/870,082, filed on Aug. 26, 2013.

(51) Int. Cl.
*A61M 29/00* (2006.01)
*A61M 25/01* (2006.01)
*A61M 25/00* (2006.01)

(52) U.S. Cl.
CPC ..... *A61M 29/00* (2013.01); *A61M 2025/0018* (2013.01); *A61M 2025/0076* (2013.01); *A61M 2025/0183* (2013.01); *A61M 2210/12* (2013.01)

(58) Field of Classification Search
CPC .. A61M 2025/0018; A61M 2025/0183; A61M 2025/0008; A61M 2025/018; A61M 29/00; A61M 25/0169; A61M 25/0172
(Continued)

(56) References Cited

U.S. PATENT DOCUMENTS 4,224,937 A 9/1980 Gordon
4,362,156 A 12/1982 Feller, Jr. et al.
(Continued)

FOREIGN PATENT DOCUMENTS

FR 2719224 11/1995
WO WO2009045276 4/2009
(Continued)

OTHER PUBLICATIONS

European Search Report dated Mar. 24, 2017 for EP14841146.5.
(Continued)

*Primary Examiner* — Diane D Yabut
*Assistant Examiner* — Majid Jamialahmadi
(74) *Attorney, Agent, or Firm* — Stoel Rives LLP

(57) ABSTRACT

Dilators, such as rapid exchange dilators, configured for percutaneous access are disclosed. The dilator may be configured to be disposable within, or couplable with, a catheter. In some embodiments, the dilator, or the coupled dilator and the catheter, may be configured such that a sheath is not required for percutaneous access. In other embodiments, the dilator may comprise a plug such that a guide wire may be directed from a distal end of the dilator through a port, such as a rapid exchange port, in a sidewall of the dilator. The plug may also be configured to permit passage of fluid through a lumen of the dilator while inhibiting passage of the guide wire through a length of the dilator.

16 Claims, 20 Drawing Sheets

(58) Field of Classification Search
USPC .................................................... 606/194
See application file for complete search history.

(56) References Cited

U.S. PATENT DOCUMENTS

| | | | |
|---|---|---|---|
| 4,705,511 A | 10/1987 | Kocak | |
| 4,748,982 A | 6/1988 | Horzewski et al. | |
| 4,798,193 A | 1/1989 | Giesy et al. | |
| 4,824,435 A | 4/1989 | Giesy et al. | |
| 4,844,092 A | 7/1989 | Rydell et al. | |
| 4,862,891 A | 9/1989 | Smith | |
| 4,976,689 A | 12/1990 | Buchbinder et al. | |
| 4,997,421 A | 3/1991 | Palsrok et al. | |
| 5,035,686 A | 7/1991 | Crittenden et al. | |
| 5,040,548 A | 8/1991 | Yock | |
| 5,061,273 A | 10/1991 | Yock | |
| 5,069,674 A | 12/1991 | Fearnot et al. | |
| 5,135,535 A | 8/1992 | Kramer | |
| 5,149,330 A | 9/1992 | Brightbill | |
| 5,154,725 A | 10/1992 | Leopold | |
| 5,180,376 A | 1/1993 | Fischell | |
| 5,324,262 A | 6/1994 | Fischell et al. | |
| 5,324,269 A | 6/1994 | Miraki | |
| 5,360,432 A | 11/1994 | Shtruman | |
| 5,364,376 A * | 11/1994 | Horzewski | A61M 25/0172 604/247 |
| 5,413,562 A | 5/1995 | Swauger | |
| 5,417,669 A | 5/1995 | Castaneda et al. | |
| 5,423,774 A | 6/1995 | Fischell et al. | |
| 5,443,457 A | 8/1995 | Ginn et al. | |
| 5,454,795 A | 10/1995 | Samson | |
| 5,484,425 A | 1/1996 | Fischell et al. | |
| 5,496,344 A | 3/1996 | Kanesaka et al. | |
| 5,514,236 A | 5/1996 | Avellanet et al. | |
| 5,531,721 A | 7/1996 | Pepin et al. | |
| 5,630,806 A | 5/1997 | Inagaki et al. | |
| 5,700,253 A | 12/1997 | Parker | |
| 5,702,373 A | 12/1997 | Samson | |
| 5,704,926 A | 1/1998 | Sutton | |
| 5,796,044 A | 8/1998 | Cobian et al. | |
| 5,827,230 A | 10/1998 | Bierman | |
| 5,827,239 A | 10/1998 | Dillon et al. | |
| 5,830,221 A | 11/1998 | Stein et al. | |
| 5,830,227 A | 11/1998 | Fischell et al. | |
| 5,849,016 A | 12/1998 | Suhr | |
| 5,863,366 A | 1/1999 | Snow | |
| 5,879,499 A | 3/1999 | Corvi | |
| 5,927,345 A | 7/1999 | Samson | |
| 5,944,697 A | 8/1999 | Biche | |
| 5,976,120 A | 11/1999 | Chow et al. | |
| 5,976,154 A | 11/1999 | Suhr | |
| 6,007,522 A | 12/1999 | Argo et al. | |
| 6,036,715 A | 3/2000 | Yock | |
| 6,066,114 A | 5/2000 | Goodin et al. | |
| 6,152,910 A | 11/2000 | Agro et al. | |
| 6,152,912 A | 11/2000 | Jansen et al. | |
| 6,165,163 A | 12/2000 | Chien et al. | |
| 6,338,725 B1 | 1/2002 | Hermann et al. | |
| 6,533,770 B1 | 3/2003 | Lepulu et al. | |
| 6,863,674 B2 | 3/2005 | Kasahara et al. | |
| 6,939,337 B2 | 9/2005 | Parker et al. | |
| 7,083,588 B1 | 8/2006 | Schmulewitz et al. | |
| 7,320,697 B2 | 1/2008 | Demond et al. | |
| 7,331,966 B2 | 2/2008 | Soma et al. | |
| 7,438,712 B2 | 10/2008 | Chouinard | |
| 7,618,430 B2 | 11/2009 | Scheib | |
| 7,655,021 B2 | 2/2010 | Brasington et al. | |
| 7,727,251 B2 | 6/2010 | Spurchise et al. | |
| 7,815,762 B2 | 10/2010 | Lentz et al. | |
| 7,905,877 B1 | 3/2011 | Jimenez et al. | |
| 8,034,045 B1 | 10/2011 | Lyons | |
| 8,262,625 B1 | 9/2012 | Fischell et al. | |
| 8,747,428 B2 | 6/2014 | Fischell et al. | |
| 2001/0010247 A1 | 8/2001 | Snow | |
| 2001/0044633 A1 | 11/2001 | Klint | |
| 2001/0049517 A1 | 12/2001 | Zadno-Azizi et al. | |
| 2001/0056285 A1 | 12/2001 | Dutta et al. | |
| 2002/0058963 A1 | 5/2002 | Vale et al. | |
| 2002/0169377 A1 | 11/2002 | Khairkhanan et al. | |
| 2003/0093060 A1 | 5/2003 | Kempf | |
| 2003/0153934 A1 * | 8/2003 | Gerberding | A61B 17/1214 606/157 |
| 2003/0199826 A1 | 10/2003 | Windheuser et al. | |
| 2003/0225365 A1 | 12/2003 | Greff et al. | |
| 2003/0229313 A1 | 12/2003 | Bierman | |
| 2004/0010243 A1 | 1/2004 | Klint | |
| 2004/0116960 A1 | 6/2004 | Demond et al. | |
| 2004/0153049 A1 | 8/2004 | Hewitt et al. | |
| 2004/0236346 A1 | 11/2004 | Parker | |
| 2005/0021022 A1 | 1/2005 | Sturm et al. | |
| 2005/0060017 A1 | 3/2005 | Fischell et al. | |
| 2005/0124939 A1 | 6/2005 | Konstantino | |
| 2005/0149060 A1 | 7/2005 | Thorstenson et al. | |
| 2005/0228479 A1 | 10/2005 | Pavcnik et al. | |
| 2006/0064054 A1 | 3/2006 | Sakakine et al. | |
| 2006/0089618 A1 | 4/2006 | McFerran et al. | |
| 2006/0095050 A1 | 5/2006 | Hartley et al. | |
| 2006/0155302 A1 | 7/2006 | Sisken et al. | |
| 2007/0066958 A1 | 3/2007 | Wright | |
| 2007/0118207 A1 | 5/2007 | Amplatz et al. | |
| 2007/0185521 A1 * | 8/2007 | Bui | A61M 25/0662 606/191 |
| 2007/0219500 A1 | 9/2007 | Wright et al. | |
| 2008/0051758 A1 | 2/2008 | Rioux et al. | |
| 2008/0097516 A1 | 4/2008 | Chang et al. | |
| 2008/0188804 A1 | 8/2008 | Jordan et al. | |
| 2009/0018525 A1 | 1/2009 | Waite et al. | |
| 2009/0054845 A1 | 2/2009 | Puhasmagi et al. | |
| 2009/0088790 A1 | 4/2009 | Parodi et al. | |
| 2009/0157162 A1 | 6/2009 | Chow et al. | |
| 2009/0182200 A1 * | 7/2009 | Golden | A61M 25/0043 600/153 |
| 2009/0234295 A1 | 9/2009 | Lampropoulos et al. | |
| 2009/0240202 A1 | 9/2009 | Drasler et al. | |
| 2009/0270815 A1 * | 10/2009 | Stamp | A61M 25/0075 604/249 |
| 2009/0287182 A1 | 11/2009 | Bishop et al. | |
| 2009/0306591 A1 | 12/2009 | Amisar et al. | |
| 2009/0306603 A1 | 12/2009 | Bierman et al. | |
| 2010/0016837 A1 | 1/2010 | Howat | |
| 2010/0049168 A1 | 2/2010 | Parker et al. | |
| 2010/0094257 A1 * | 4/2010 | Stalker | A61M 25/0041 604/524 |
| 2011/0160702 A1 | 6/2011 | Jimenez et al. | |
| 2011/0245775 A1 | 10/2011 | Tekulve | |
| 2012/0215174 A1 | 8/2012 | Fischell et al. | |
| 2012/0265282 A1 | 10/2012 | Fischell et al. | |
| 2013/0131718 A1 | 5/2013 | Jenson et al. | |
| 2013/0184735 A1 | 7/2013 | Fischell et al. | |

FOREIGN PATENT DOCUMENTS

| | | |
|---|---|---|
| WO | 2009127216 | 10/2009 |
| WO | 2015031252 | 3/2015 |

OTHER PUBLICATIONS

U.S. Appl. No. 14/297,903, filed Jun. 6, 2014, Fischell et al.
Notice of Allowance dated Feb. 28, 2014 for U.S. Appl. No. 13/349,060.
International Search Report and Written Opinion dated Apr. 25, 2013 for PCT/US2013/020941.
Office Action dated Jun. 3, 2013 for U.S. Appl. No. 13/349,060.
Office Action dated Oct. 29, 2013 for U.S. Appl. No. 13/349,060.
Office Action dated Jan. 26, 2015 for U.S. Appl. No. 14/297,903.
Extended European Search Report dated Jul. 1, 2015 for EP13735804.0.
International Search Report and Written Opinion dated Nov. 28, 2014 for PCT/US2014/052520.

(56) References Cited

OTHER PUBLICATIONS

Notice of Allowance dated Jun. 10, 2015 for U.S. Appl. No. 14/297,903.

* cited by examiner

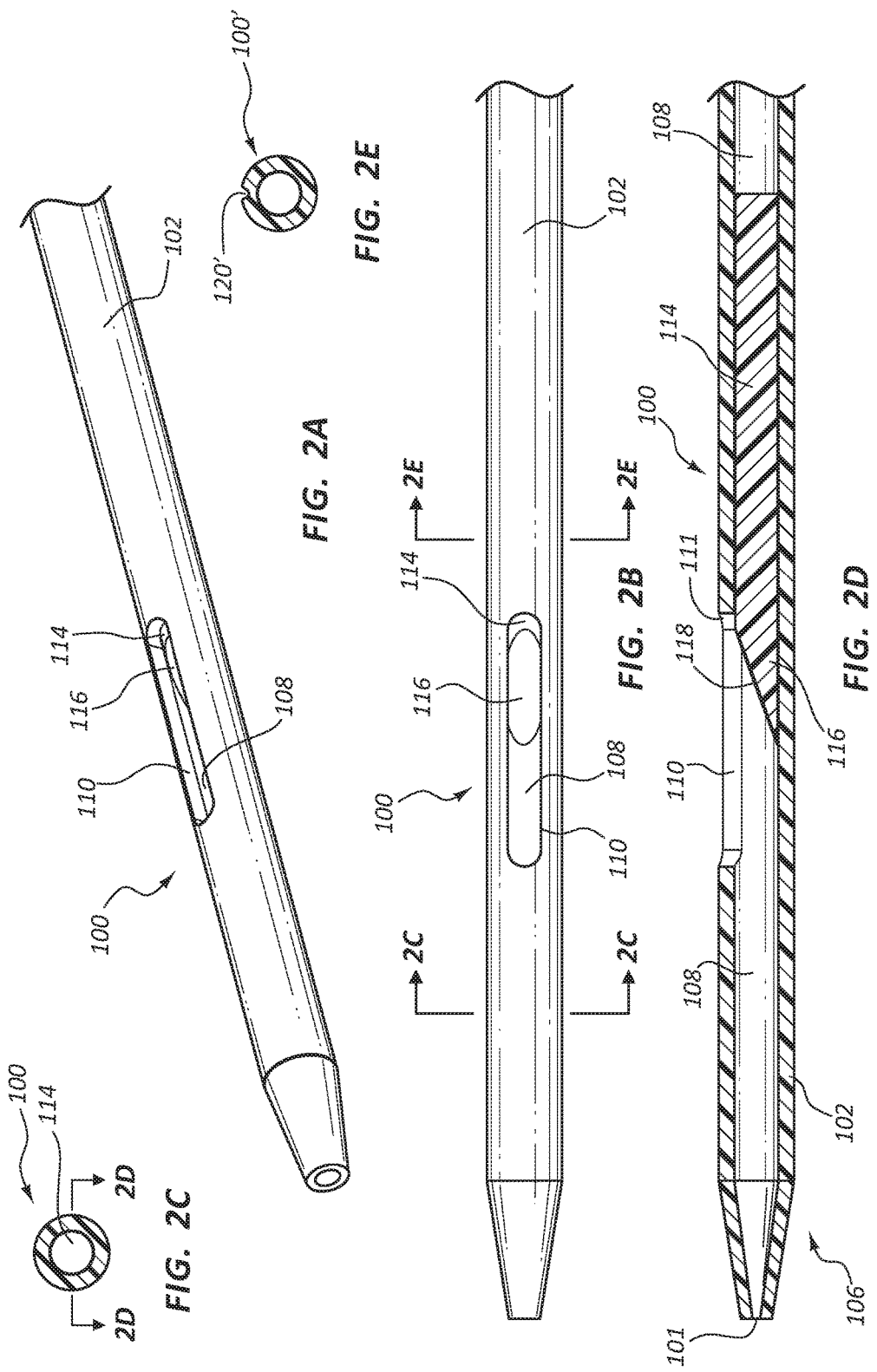

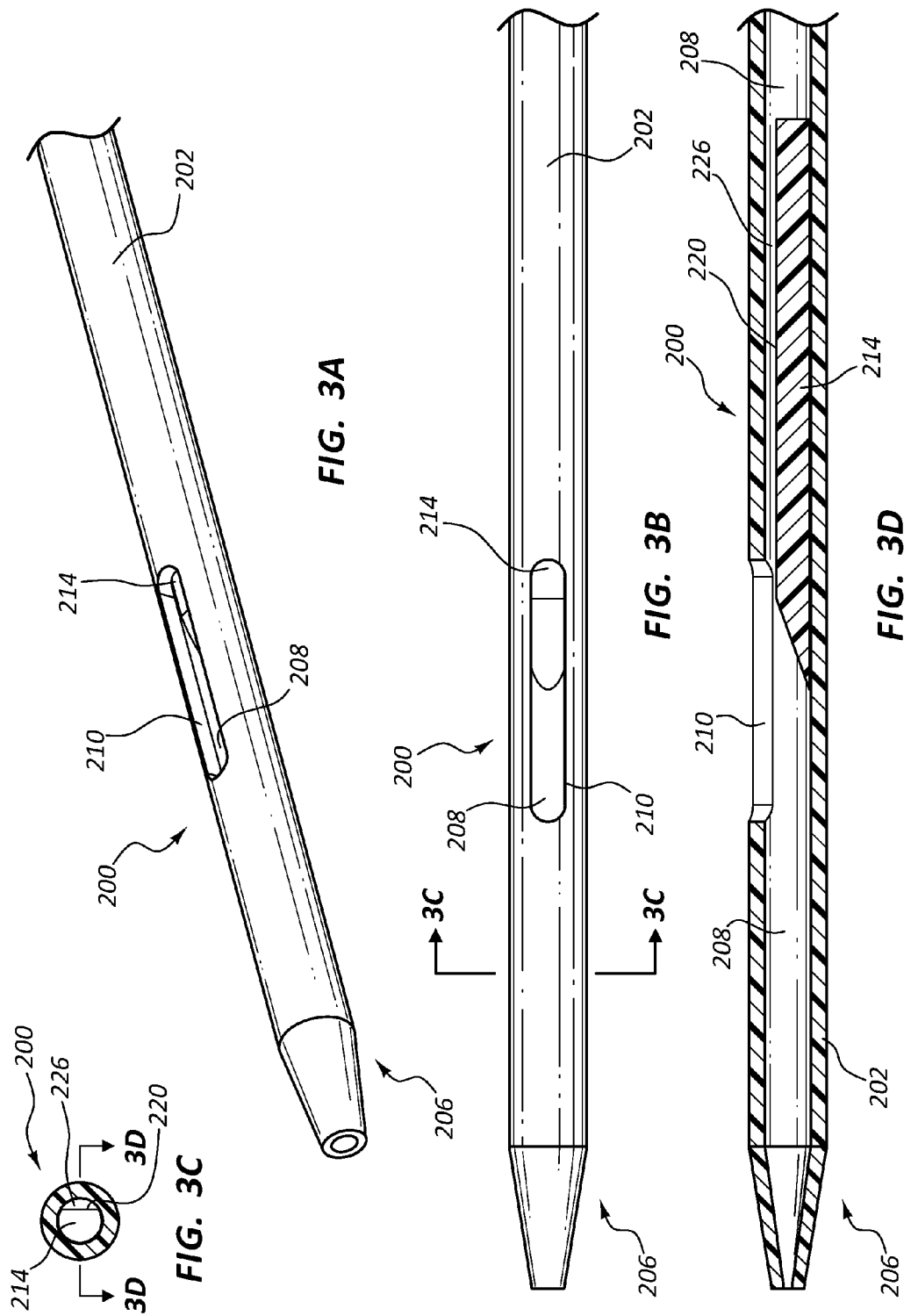

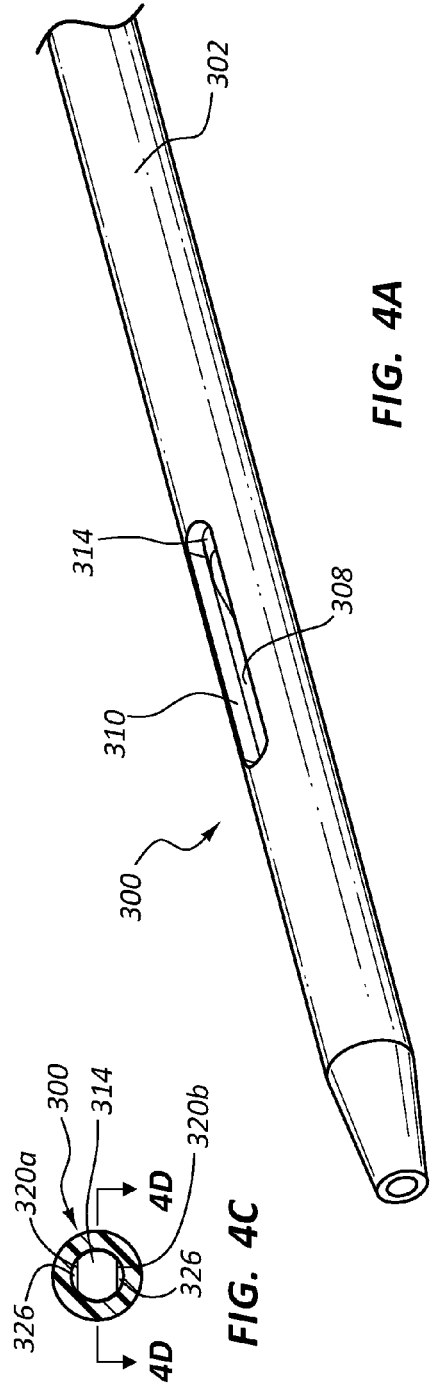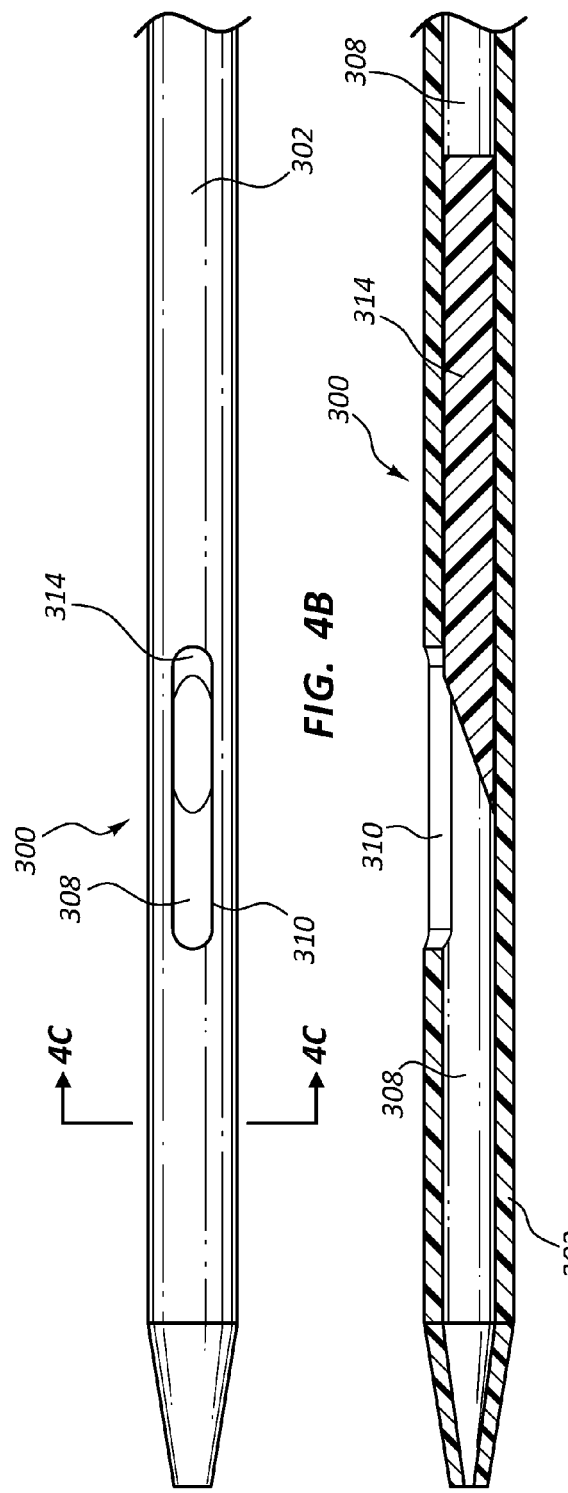

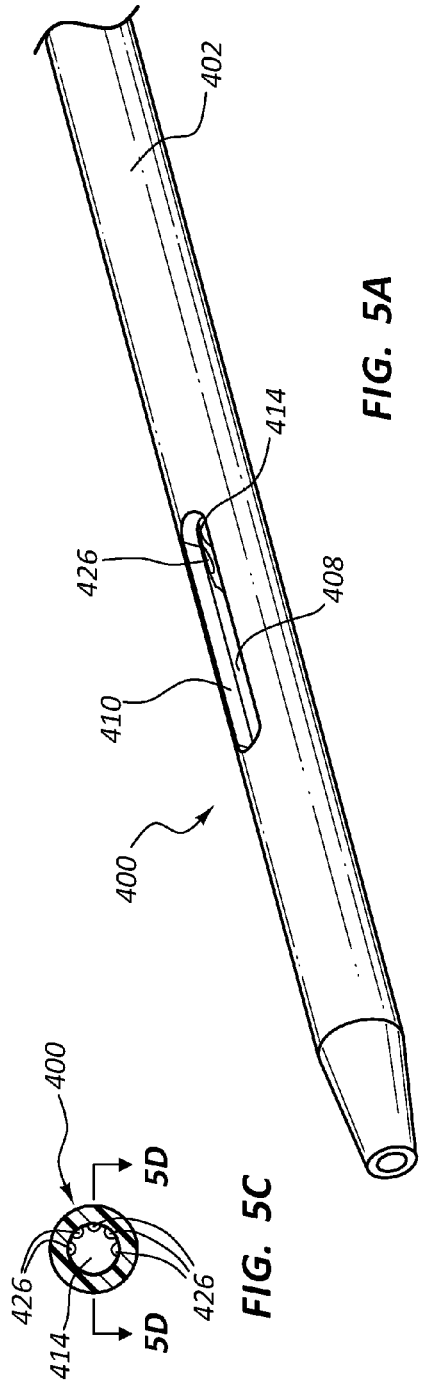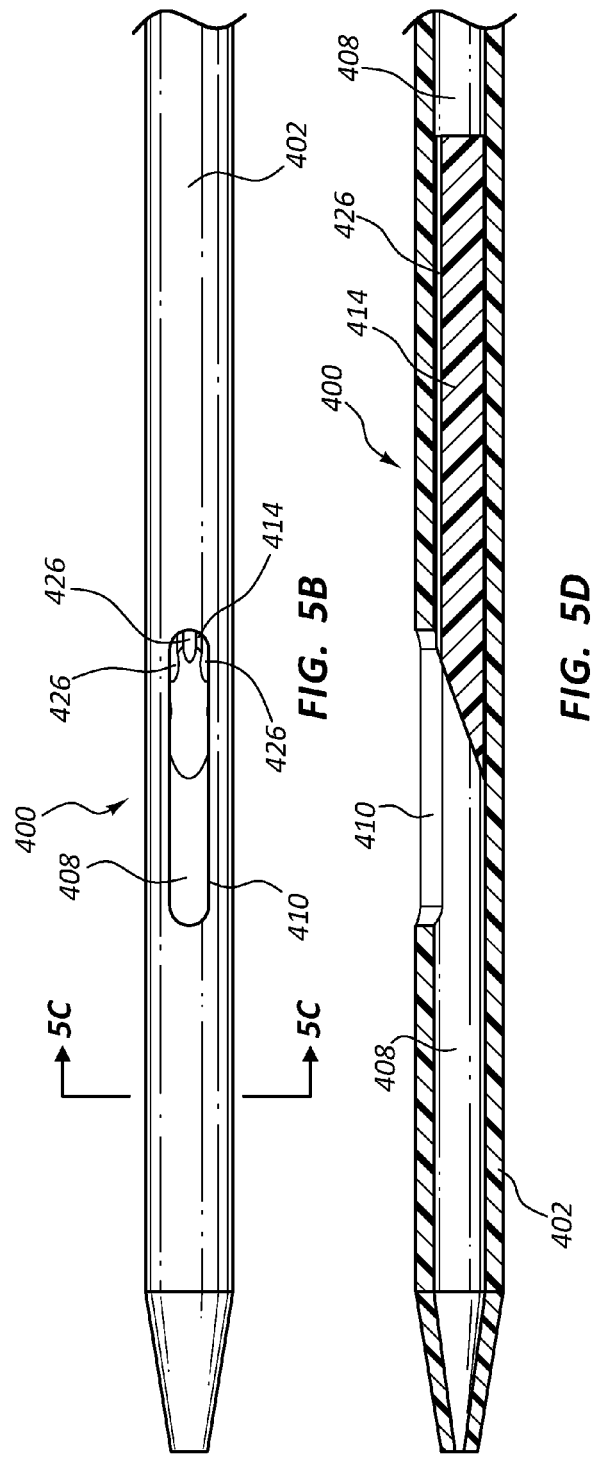

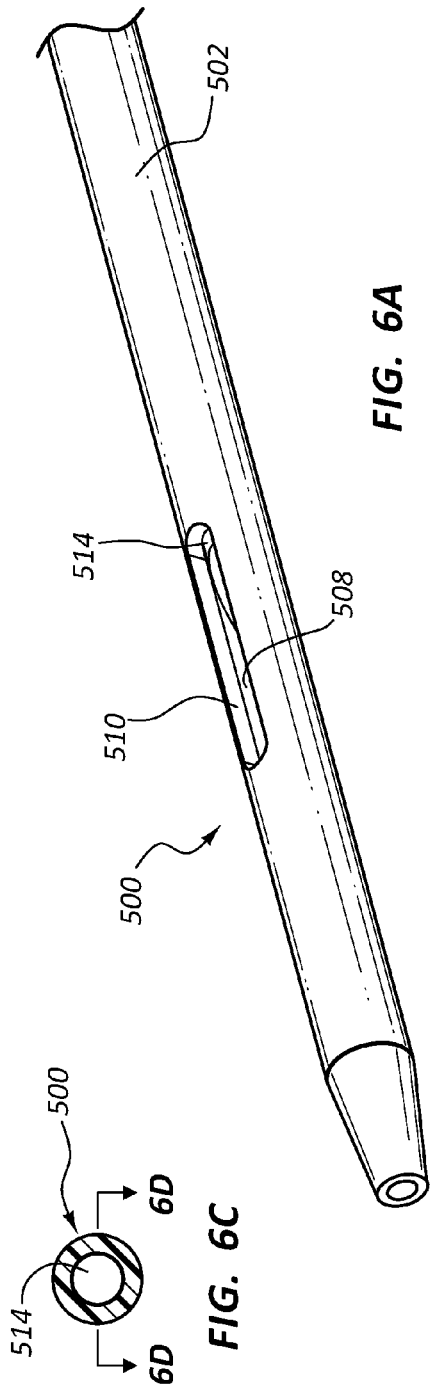
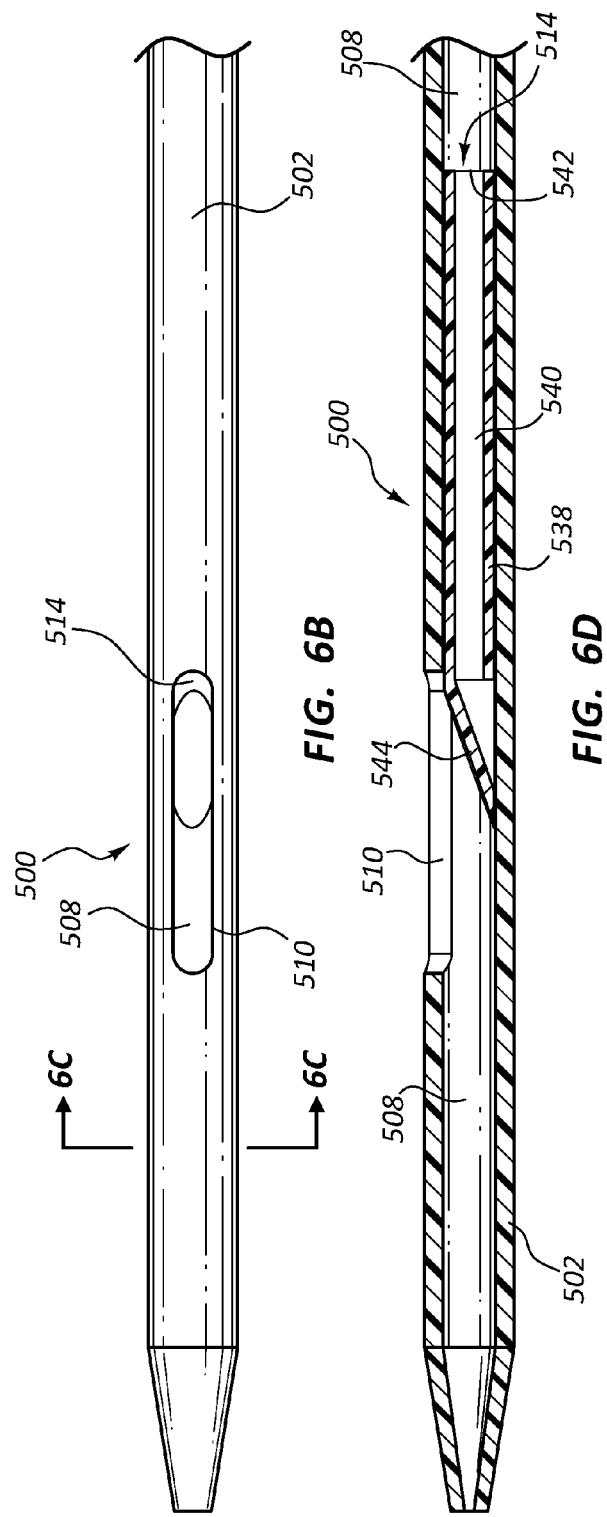

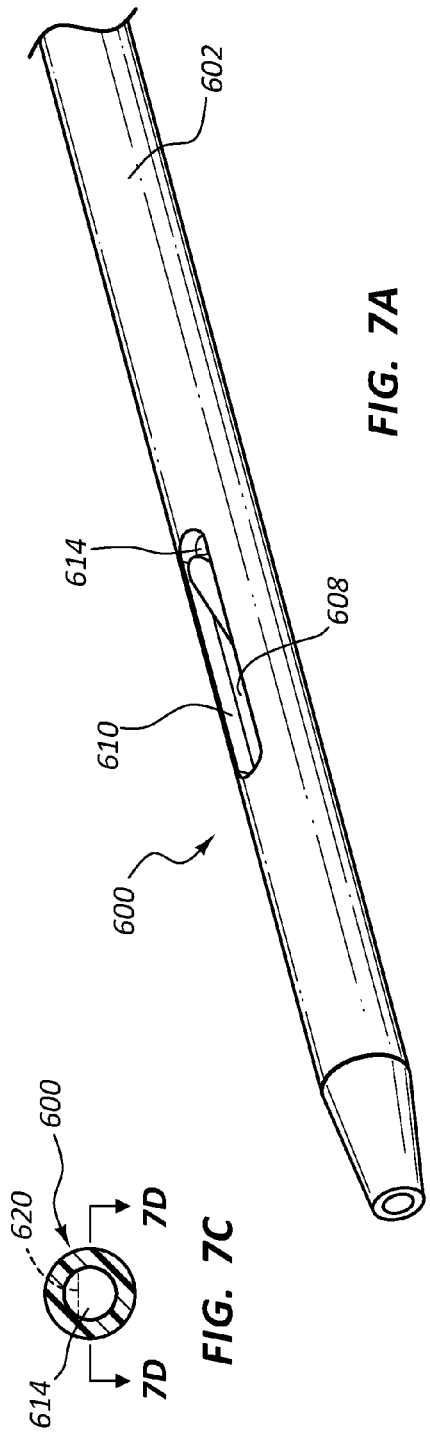
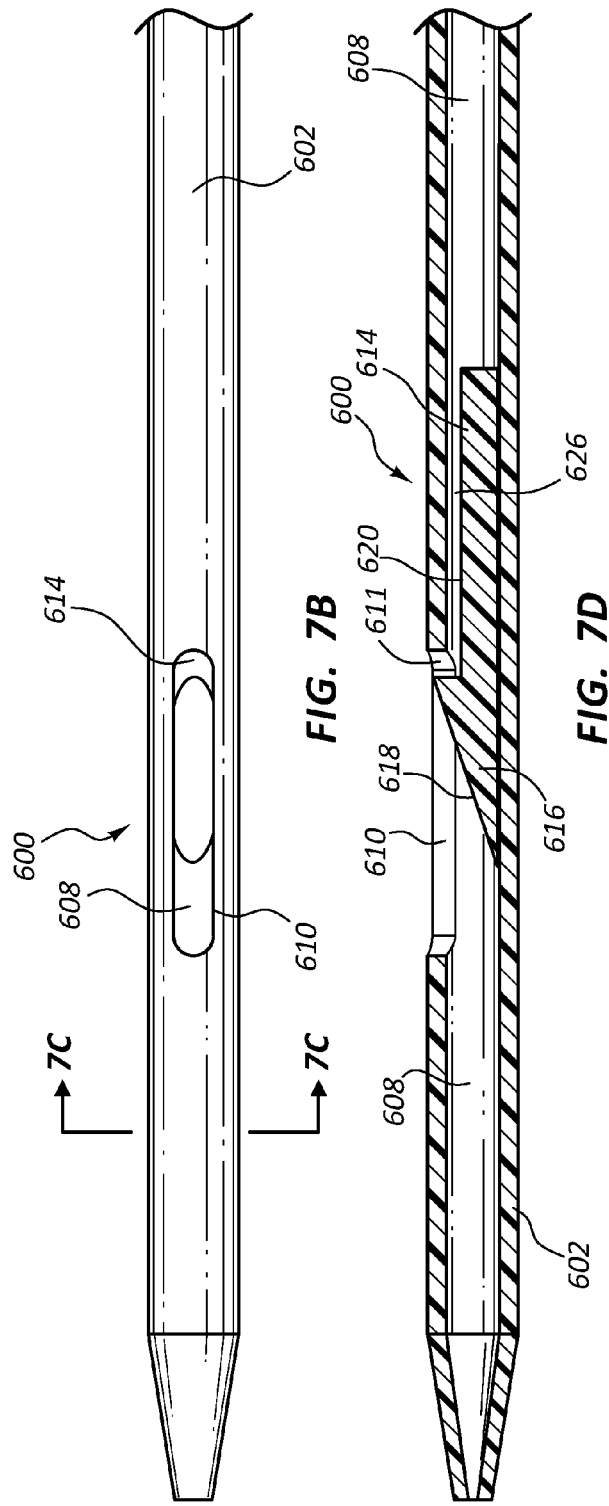
FIG. 7A
FIG. 7B
FIG. 7C
FIG. 7D

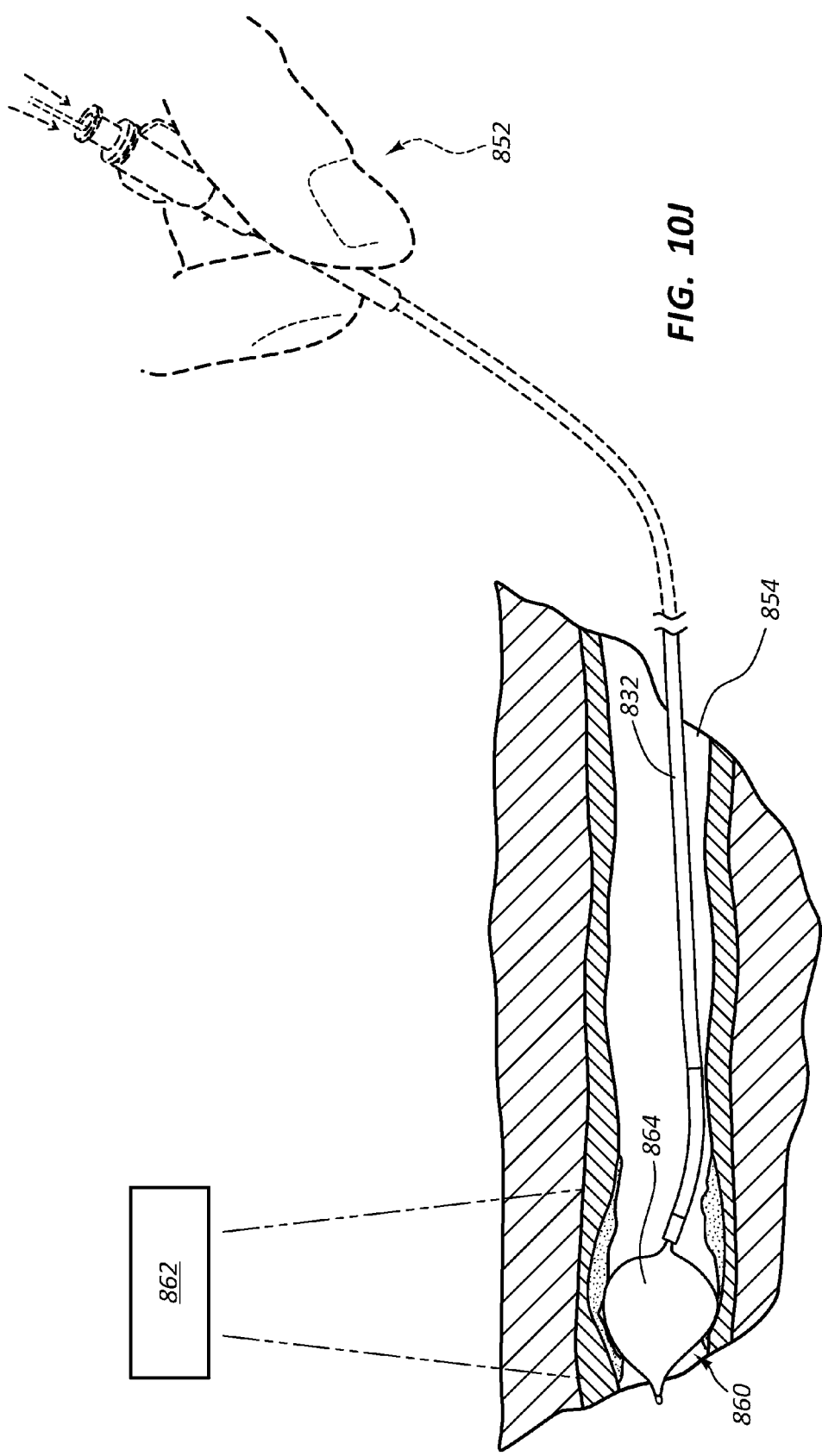

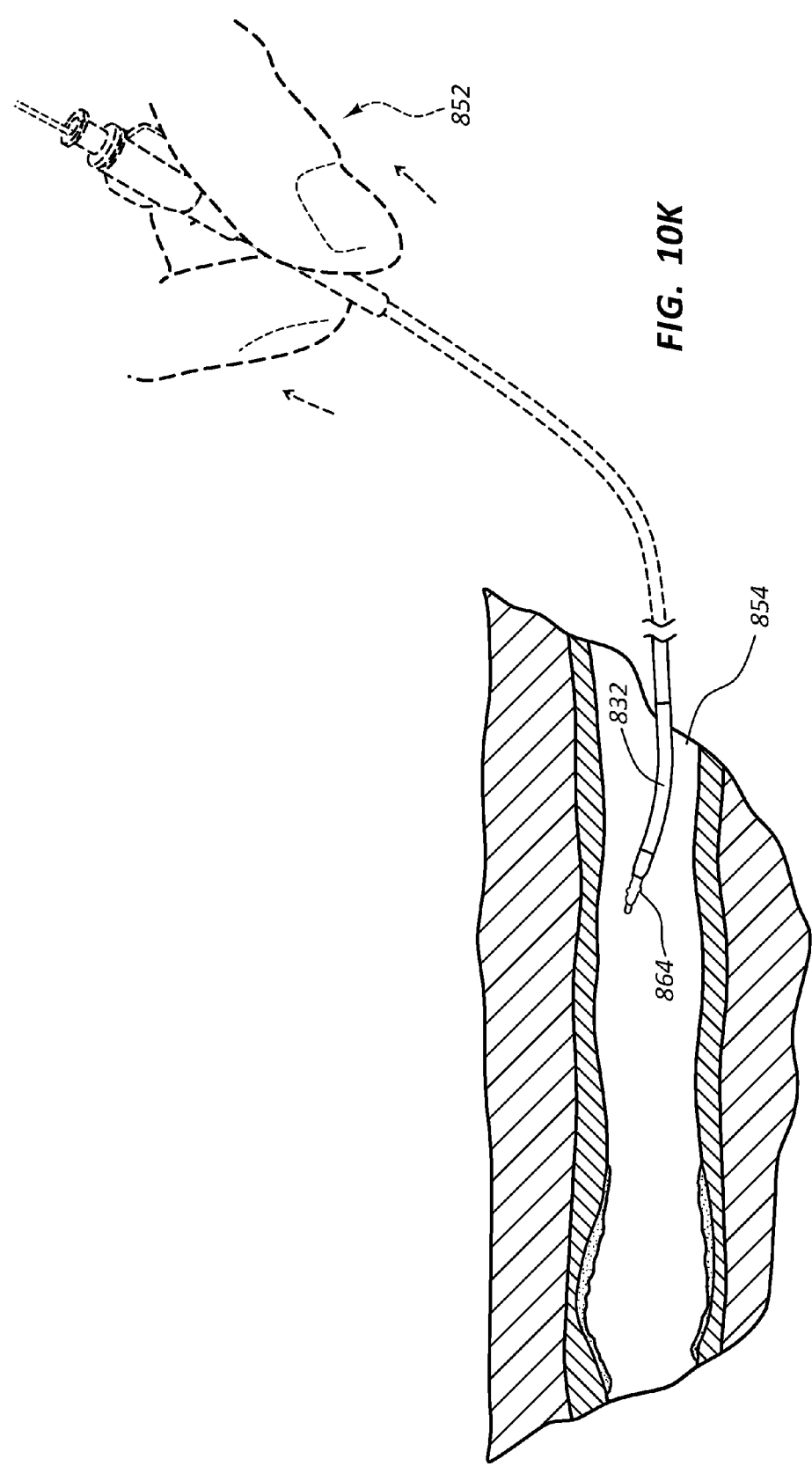

SHEATHLESS GUIDE, RAPID EXCHANGE DILATOR AND ASSOCIATED METHODS

This application claims priority to U.S. Provisional Application No. 61/870,082, filed on Aug. 26, 2013 and titled "Rapid Exchange Dilator and Associated Methods," which is hereby incorporated by reference in its entirety.

TECHNICAL FIELD

The present disclosure relates generally to dilators configured for percutaneous access. The disclosed dilators may also be disposable in, and/or couplable with, catheters for use during vascular procedures.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 2A is a perspective view of a distal portion of the dilator of FIG. 1.

FIG. 2B is a top view of the distal portion of the dilator of FIG. 1.

FIG. 2C is a cross-sectional view of the portion of the dilator of FIG. 2B taken through line 2C-2C.

FIG. 2D is a cross-sectional view of the portion of the dilator of FIG. 2C taken through line 2D-2D.

FIG. 2E is a cross-sectional view of another embodiment of a dilator, taken through a plane analogous to plane 2E-2E as shown on the dilator of the embodiment of FIG. 2B.

FIG. 3A is a perspective view of a distal portion of a second embodiment of a dilator.

FIG. 3B is a top view of the portion of the dilator of FIG. 3A.

FIG. 3C is a cross-sectional view of the portion of the dilator of FIG. 3B taken through line 3C-3C.

FIG. 3D is a cross-sectional view of the portion of the dilator of FIG. 3C taken through line 3D-3D.

FIG. 4A is a perspective view of a distal portion of a third embodiment of a dilator.

FIG. 4B is a top view of the portion of the dilator of FIG. 4A.

FIG. 4C is a cross-sectional view of the portion of the dilator of FIG. 4B taken through line 4C-4C.

FIG. 4D is a cross-sectional view of the portion of the dilator of FIG. 4C taken through line 4D-4D.

FIG. 5A is a perspective view of a distal portion of a fourth embodiment of a dilator.

FIG. 5B is a top view of the portion of the dilator of FIG. 5A.

FIG. 5C is a cross-sectional view of the portion of the dilator of FIG. 5B taken through line 5C-5C.

FIG. 5D is a cross-sectional view of the portion of the dilator of FIG. 5C taken through line 5D-5D.

FIG. 6A is a perspective view of a distal portion of a fifth embodiment of a dilator.

FIG. 6B is a top view of the portion of the dilator of FIG. 6A.

FIG. 6C is a cross-sectional view of the portion of the dilator of FIG. 6B taken through line 6C-6C.

FIG. 6D is a cross-sectional view of the portion of the dilator of FIG. 6C taken through line 6D-6D.

FIG. 7A is a perspective view of a distal portion of a sixth embodiment of a dilator.

FIG. 7B is a top view of the portion of the dilator of FIG. 7A.

FIG. 7C is a cross-sectional view of the portion of the dilator of FIG. 7B taken through line 7C-7C.

FIG. 7D is a cross-sectional view of the portion of the dilator of FIG. 7C taken through line 7D-7D.

FIG. 10J is a view showing performance and visualization of the performance of a vascular procedure at the therapy site.

FIG. 10K is a view showing removal of the catheter from the vessel.

DETAILED DESCRIPTION

Figure 1:
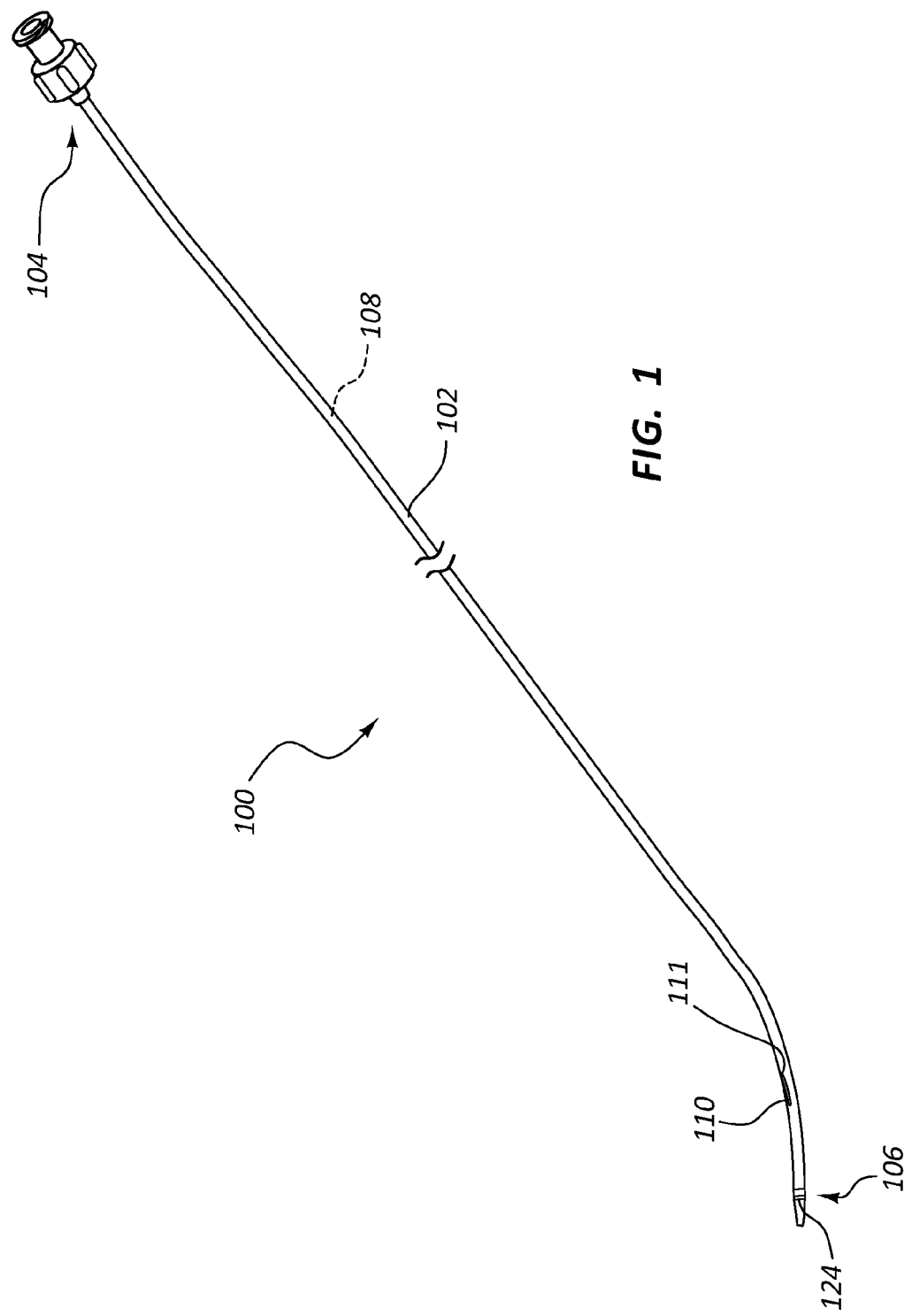
FIG. 1 is a perspective view of a first embodiment of a dilator.

A dilator may be configured for percutaneous access. Percutaneous access may be made at an artery, such as the brachial artery, femoral artery, radial artery, carotid artery; a vein such as the jugular vein; or another physiological feature, including other locations of the vasculature. The dilator may be configured to be disposable within, or couplable with, a catheter. In some embodiments, the dilator, or the coupled dilator and catheter, may be configured such that a sheath is not utilized during percutaneous access. Percutaneous access may allow introduction of a medical device into a vessel of a patient and disposition of the medical device at or adjacent a therapy site within the vessel. Introduction of a medical device into a vessel may be used for performance a vascular procedure. Medical devices that may be introduced into a vessel include, but are not limited to, atherectomy devices (i.e., rotobladers), aspirators, balloon catheters, diagnostic catheters, guiding catheters, interventional catheters, snares, and stents.

It will be readily understood by one of skill in the art having the benefit of this disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

As used herein, the term "dilator" refers to an elongate medical device configured to expand or enlarge an opening in a vessel as the dilator is advanced through the opening. Therefore, in some embodiments, a dilator may comprise a taper at a first end. In certain embodiments, a dilator may be utilized in combination with a catheter and/or sheath. A dilator may also be stiffer than a catheter and/or sheath. A relatively stiff dilator may be configured to facilitate advancement of a relatively flexible catheter through the wall of a body lumen. Still further, a tapered dilator may be configured to provide a smooth transition between the outside diameter of a guide wire and the outside diameter of a catheter (and/or sheath) as the dilator and catheter (and/or sheath) is advanced along the guide wire into a body lumen.

The terms "proximal" and "distal" refer to opposite ends of a medical device. With respect to dilators and vascular access systems disclosed herein, the proximal end refers to the end nearest a practitioner when the device is in use.

FIG. 1 is perspective view of a first embodiment of a dilator 100, which may be configured as a rapid exchange dilator. In some embodiments, the dilator 100 may be flexible, plastic, and/or pliable. In the illustrated embodiment, the dilator 100 comprises an elongate member 102, wherein the elongate member 102 comprises both a proximal end 104 and a distal end 106. In some embodiments, the dilator 100 may comprise a lumen 108 disposed within at least a portion of the elongate member 102. The illustrated dilator 100 further comprises a port 110, which may be configured as a rapid exchange port, disposed in a sidewall of the elongate member 102, wherein the port 110 may be in fluid communication with the lumen 108. As illustrated, the port 110 is elongate. In other embodiments, the port 110 may be circular, rectangular, square, triangular, or otherwise shaped. Ports 110 of any size and/or shape are within the scope of this disclosure. In other embodiments, there may be more than one port 110, for example, there may be two ports, three ports, four ports, and so on. In some embodiments, the lumen 108 may extend from the proximal end 104 to the distal end 106 of the elongate member 102, or the lumen 108 may extend through only a portion of the elongate member 102. In other embodiments, there may be more than one lumen 108, for example, there may be two lumens, three lumens, four lumens, and so on.

In some embodiments, at least a portion of the dilator 100 may be radiopaque. For example, the dilator 100 may comprise one or more radiopaque bands 124. The radiopaque bands 124 may assist a practitioner in determining and/or visualizing the location or position of the dilator 100 within a patient. For example, the practitioner may use a fluoroscope, or other imaging device, to visualize the location of the dilator 100 within the vasculature of the patient by locating the positions of the radiopaque bands 124. In some embodiments, the radiopaque bands 124 may be positioned at predetermined points along a length of the dilator 100. For example, a radiopaque band 124 may be positioned at or adjacent to the distal end 106 of the dilator 100 as illustrated in FIG. 1.

Also, the distal end 106 of the illustrated dilator 100 is tapered. Other configurations of the dilator 100, however, such as a dilator lacking a tapered end or a dilator comprising a longer or shorter tapered portion, are also within the scope of this disclosure. In some embodiments, at least a portion of the dilator 100 may be hydrophilic or otherwise lubricious. For example, a portion of an outside surface of the dilator 100 may be hydrophilic such that the outside surface of the dilator 100 is lubricious, slippery, and/or smooth such that the dilator 100 may be disposed or moved through a percutaneous access site and/or a tortuous and/or narrow vascular anatomy.

In some embodiments, a portion of an outside surface of the dilator 100, extending from a proximal end 111 of the port 110, may comprise a recess configured to accommodate a portion of a guide wire. Such a configuration may aid in disposition or movement of the dilator 100 in combination with a guide wire through a percutaneous access site and/or through a patient's vasculature.

An apparatus for a percutaneous access site is also within the scope of this disclosure. The apparatus may comprise an elongate member, like elongate member 102, configured for passage of a fluid or fluids through at least a portion of the elongate member. The elongate member may be further configured for passage of a guide wire through only a portion of the elongate member. In other embodiments, the elongate member may be configured for passage of a fluid or fluids along substantially an entire length of the elongate member. In some embodiments, the guide wire may be displaceable along a portion of the elongate member through a first opening of the elongate member and the elongate member may be configured to direct the guide wire out of a second opening of the elongate member. For example, the elongate member may comprise an angled guiding surface configured to direct the guide wire out of the second opening of the elongate member. In certain embodiments, the second opening may be disposed in a sidewall of the elongate member.

FIGS. 2A-2D are various views of a distal portion of the dilator 100 of FIG. 1. FIG. 2A is a perspective view of the distal portion of the dilator 100 of FIG. 1. FIG. 2B is a top view of the distal portion of the dilator 100 of FIG. 1; FIG. 2C is a cross-sectional view of the portion of the dilator 100 of FIG. 2B taken through line 2C-2C; and FIG. 2D is a cross-sectional view of the portion of the dilator 100 of FIG. 2C taken through line 2D-2D. As illustrated in FIGS. 2A-2D, the dilator 100 may further comprise a plug 114 disposed in the lumen 108, proximal to at least a portion of the port 110. In some embodiments, the plug 114 may be disposed at a position more proximal to the port 110 than is illustrated. While in other embodiments, a distal end 116 of the plug 114 may be disposed at a position more distal to a proximal end 111 of the port 110 than is illustrated.

In the illustrated embodiment of FIG. 2D, the distal end 116 of the plug 114 defines an angled surface 118 extending from a surface of the lumen 108 opposite of the port 110 to a position at or adjacent a proximal end 111 of the port 110. Stated another way, the distal end 116 of the plug 114 may be wedge-shaped. In other embodiments, the distal end 116 of the plug 114 may comprise a concave curve or a convex curve. Other configurations of the distal end 116 of the plug 114 are also within the scope of this disclosure. The angled surface 118 may be configured to direct a guide wire or other medical device advanced through an opening 101 at the distal end 106 of the elongate member 102 through the port 110. The angled surface 118 may be configured such that the guide wire or other medical device does not get caught or stuck at a junction between the plug 114 and the elongate member 102. In some embodiments, the angled surface 118 may be configured such that the guide wire or the other medical device makes a smooth transition as it moves from an interior of the dilator to an exterior of the dilator 100. In some embodiments, the guide wire or other medical device may be introduced or threaded into the dilator 100 through the port 110, into the lumen 108 of the elongate member 102, and out the opening 101 at the distal end 106 of the dilator 100. In such an embodiment, the angled surface 118 may also be configured such that the guide wire or other medical device smoothly transitions as it moves or is displaced from the exterior of the dilator 100 to the interior of the dilator 100.

The plug 114, as illustrated in FIG. 2D, is configured such that it occludes the lumen 108. In such a configuration, the dilator 100 may be configured such that fluid communication through the lumen 108 between the proximal end and the distal end 106 of the elongate member 102 is blocked, inhibited, or substantially inhibited at the plug 114.

In other embodiments, the lumen 108 may extend from the distal end 106 of the elongate member 102 to the port 110. In such embodiments, a portion of the elongate member 102 proximal to the lumen 108 may be solid. The lumen 108 may also be configured to direct a guide wire extending from the distal end 106 of the elongate member 102 through the port 110.

In certain embodiments, the plug 114 may be coupled to the elongate member 102. For example, the plug 114 may be bonded or glued to the elongate member 102. In other embodiments, the plug 114 may be integrally formed with the elongate member 102. For example, the plug 114 may be extruded and/or molded as an integral or intrinsic part of the elongate member 102.

FIG. 2E is a cross-sectional view of a dilator 100' analogous to the dilator 100 of FIGS. 2A-2B though dilator 100' comprises a recess 120' configured to accommodate a portion of a guide wire. FIG. 2E is taken though a cross-sectional plane along dilator 100' analogous to plane 2E-2E as shown on the dilator 100 of FIG. 2B.

FIGS. 3A-3D are various views of a distal portion of a second embodiment of a dilator 200. FIG. 3A is a perspective view of the distal portion of the second embodiment of the dilator 200. FIG. 3B is a top view of the portion of the dilator 200 of FIG. 3; FIG. 3C is a cross-sectional view of the portion of the dilator 200 of FIG. 3B taken through line 3C-3C; and FIG. 3D is a cross-sectional view of the portion of the dilator 200 of FIG. 3C taken through line 3D-3D. The embodiment of FIGS. 3A-3D may include components that resemble components of the embodiment of FIGS. 2A-2D in some respects. For example, the embodiment of FIG. 3A includes a dilator 200 that may resemble the dilator 100 of FIG. 2A. It will be appreciated that all the illustrated embodiments have analogous features. Accordingly, like features are designed with like reference numerals, with leading digits added to increment each reference numeral by 100. (For instance, the dilator is designated "100" in FIG. 2A and an analogous dilator is designated as "200" in FIG. 3A.) Relevant disclosure set forth above regarding similarly identified features thus may not be repeated hereafter. Moreover, specific features of the dilator shown in FIGS. 3A-3D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the dilator of FIGS. 3A-3D. Any suitable combination of the features, and variations of the same, described with respect to the dilator illustrated in FIGS. 2A-2D, can be employed with the dilator of FIGS. 3A-3D, and vice versa. This pattern of disclosure applies equally to further embodiments depicted in subsequent figures and/or described hereafter.

In the embodiment of FIGS. 3A-3D, the dilator 200 comprises a plug 214 disposed in a lumen 208 proximal to at least a portion of a port 210. In some embodiments, the plug 214 may be configured such that fluid communication is allowed or permitted between the proximal end and the distal end 206 of the elongate member 202. In the illustrated embodiment of FIGS. 3C and 3D, the plug 214 does not completely occlude the lumen 208 of the elongate member 202, in contrast to the plug 114 illustrated in FIG. 2D. The plug 214 comprises a substantially planar first surface 220. The first surface 220, as illustrated, provides a recess in the plug 214 such that a gap 226, or fluid passage, is present between the first surface 220 of the plug 214 and a portion of the inside surface of the lumen 208. In some embodiments, a portion of an outside surface of the plug 214 may comprise one or more recesses such that one or more gaps 226 are formed or present between the portion of the outside surface of the plug 214 and a portion of the surface of the lumen 208. The gap 226 formed or created by the first planar surface 220 may be further configured such that passage of a guide wire through the gap 226 is not allowed or permitted. For example, the size of the gap 226 may be such that the gap 226 is too small to allow or permit passage of a guide wire. The gap 226 may also be configured such that upon threading of a distal end of a guide wire through the lumen 208 and/or the port 210 of the dilator 200, the distal end of the guide wire does not get caught or stuck at or adjacent an entrance of the gap 226. In some embodiments, a practitioner may flush a dilator comprising one or more gaps 226 with a saline solution, a heparinized saline solution, water, and/or another physiologically compatible sterile fluid prior to use, or during use, of the dilator.

As described above for the plug 114, the plug 214 may be coupled to the elongate member 202. For example, the plug 214 may be bonded or glued to the elongate member 202. In other embodiments, the plug 214 may be integrally formed with the elongate member 202. For example, the plug 214 may be extruded and/or molded as an integral or intrinsic part of the elongate member 202.

FIGS. 4A-4D are various views of a distal portion of a third embodiment of a dilator 300. FIG. 4A is a perspective view of a distal portion of the third embodiment of the dilator 300. FIG. 4B is a top view of the portion of the dilator 300 of FIG. 4A; FIG. 4C is a cross-sectional view of the portion of the dilator 300 of FIG. 4B taken through line 4C-4C; and FIG. 4D is a cross-sectional view of the portion of the dilator 300 of FIG. 4C taken through line 4D-4D. In the embodiment of FIGS. 4A-4D, the illustrated dilator 300 comprises a plug 314 disposed in a lumen 308 proximal to at least a portion of a port 310. Again, in some embodiments, such as illustrated in FIGS. 3C and 3D, a plug may be configured such that fluid communication is permitted between the proximal end and the distal end of the elongate member. Likewise, in the illustrated embodiment of FIG. 4C, the plug 314 does not block or completely occlude the lumen of the elongate member, in contrast to the plug 114 of FIGS. 2A-2D.

The illustrated plug 314 comprises a substantially planar first surface 320a and a substantially planar second surface 320b (FIG. 4C). Both of the first surface 320a and the second surface 320b, as illustrated, provide recesses in the plug 314 such that gaps 326, or fluid passages, are formed or present between both of the first surface 320a and the second surface 320b of the plug 314 and portions of the inside surface of the lumen. In some embodiments, a portion or portions of an outside surface of the plug 314 may comprise a plurality of recesses such that a plurality of gaps 326 are formed or present between portions of the outside surface of the plug 314 and portions of the surface of the lumen. The gaps 326 created by the first and second planar surfaces 320a, 320b may be configured such that passage of a guide wire through the gaps 326 is not allowed or permitted. For example, the size of the gaps 326 may be such that the gaps 326 are too small to allow or permit passage of a guide wire. The gaps 326 created by the first and second planar surfaces 320a, 320b may also be configured such that upon threading of a distal end of a guide wire through the lumen of the dilator and/or through the port, the guide wire does not get caught or stuck at or adjacent an entrance to one or more of the gaps.

As described above for other embodiments of the plug, the plug 314 may be coupled to the elongate member 302 (FIGS. 4A, 4B, and 4D). For example, the plug 314 may be bonded or glued to the elongate member 302. In other embodiments, the plug 314 may be integrally formed with the elongate member 302. For example, the plug 314 may be extruded and/or molded as an integral or intrinsic part of the elongate member 302.

FIGS. 5A-5D are various views of a distal portion of a fourth embodiment of a dilator 400. FIG. 5A is a perspective view of a distal portion of the fourth embodiment of the dilator 400. FIG. 5B is a top view of the portion of the dilator 400 of FIG. 5A; FIG. 5C is a cross-sectional view of the portion of the dilator 400 of FIG. 5B taken through line 5C-5C; and FIG. 5D is a cross-sectional view of the portion of the dilator 400 of FIG. 5C taken through line 5D-5D. In the embodiment of FIGS. 5A-5D, the dilator 400 comprises a plug 414 disposed in a lumen 408 proximal to at least a portion of a port 410. Again, in some embodiments, such as illustrated in FIGS. 3C and 3D, a plug may be configured such that fluid communication is permitted between the proximal end and the distal end of the elongate member. Likewise, in the illustrated embodiment of FIGS. 5A-5D, the plug 414 does not completely occlude the lumen 408 of the elongate member 402, in contrast to the plug 114 of FIGS. 2A-2D. The illustrated plug 414 is at least partially fluted on a portion of an outside surface of the plug 414. As illustrated, the plurality of flutes provide a plurality of recesses in the plug 414 such that a plurality of gaps 426, or fluid passages, are formed or present between a portion of the outside surface of the plug 414 and a portion of the inside surface of the lumen 408. As illustrated, each gap 426 of the fluted plug 414 is substantially semicircular. In other embodiments, the gaps 426 may be ovoid, square, and/or triangular. Other shapes, or combinations of shapes, of gaps 426 are also contemplated. The gaps 426 may be configured such that passage of a guide wire through the gaps 426 is not allowed or permitted. For example, the size of the gaps 426 may be such that the gaps 426 are too small to allow or permit passage of a guide wire. The gaps 426 may also be configured such that upon threading of a guide wire through the lumen 408 of the dilator 400 and/or through the port 410 of the dilator 400, the distal end of the guide wire does not get caught or stuck at or adjacent an entrance of one or more of the gaps 426. In other embodiments, the plug 414 may comprise a hole or holes passing through an interior of the plug 414 as opposed to a gap or gaps 426 passing along the outside surface of the plug 414.

As described above for other embodiments of the plug, the plug 414 may be coupled to the elongate member 402. For example, the plug 414 may be bonded or glued to the elongate member 402. In other embodiments, the plug 414 may be integrally formed with the elongate member 402. For example, the plug 414 may be extruded and/or molded as an integral or intrinsic part of the elongate member 402.

FIGS. 6A-6D are various views of a distal portion of a fifth embodiment of a dilator 500. FIG. 6A is a perspective view of a distal portion of the fifth embodiment of the dilator 500. FIG. 6B is a top view of the portion of the dilator 500 of FIG. 6A; FIG. 6C is a cross-sectional view of the portion of the dilator 500 of FIG. 6B taken through line 6C-6C; and FIG. 6D is a cross-sectional view of the portion of the dilator 500 of FIG. 6C taken through line 6D-6D. In the embodiment of FIGS. 6A-6D, the dilator 500 comprises a plug 514 disposed in a lumen 508 proximal to at least a portion of a port 510. Again, in some embodiments, such as illustrated in FIGS. 3C and 3D, a plug may be configured such that fluid communication is permitted between the proximal end and the distal end of the elongate member. Likewise, in the embodiment of FIGS. 6A-6D, the plug 514 is configured to not completely occlude the lumen 508 of the elongate member 502, in contrast to the plug 114 of FIGS. 2A-2D. The illustrated plug 514 comprises an elongate member 538 and a lumen 540, or fluid passage, disposed longitudinally within the elongate member 538 (FIG. 6D). The plug 514 further comprises an opening 542 at or adjacent a proximal end of the plug 514. At a distal end of the plug 514 an upper sidewall of the plug 514 extends distally in relation to a lower sidewall of the plug 514. The extension of the upper sidewall of the plug 514 defines an angled surface extending from a surface of the lumen 508 at or adjacent the port 510 to a surface of the lumen 508 opposite of the port 510 forming a check valve 544. A distal end of the check valve 544 is not bonded or fixed to the elongate member 502. The check valve 544 may transition from a closed configuration, as illustrated in FIG. 6D, to an open configuration when, for example, a practitioner flushes a saline solution, a heparinized saline solution, water, and/or another sterile physiologically compatible fluid through the lumen 508 of the dilator 500. Fluid pressure distal of the plug 514 may open the check valve 544 while the check valve 544 may return to a closed configuration upon removal of a fluid pressure from the lumen 508.

As illustrated, the check valve 544 may also be configured such that upon threading of a guide wire through the lumen 508 of the dilator and/or through the port 510, the distal end of the guide wire does not get caught or stuck at or adjacent a junction of the plug 514 and the elongate member 502.

As described above for other embodiments of the plug, the plug 514 may be coupled to the elongate member 502. For example, the plug 514 may be bonded or glued to the elongate member 502. In other embodiments, the plug 514 may be integrally formed with the elongate member 502. For example, the plug 514 may be extruded and/or molded as an integral or intrinsic part of the elongate member 502.

FIGS. 7A-7D are various views of a distal portion of a sixth embodiment of a dilator 600. FIG. 7A is a perspective view of the distal portion of the sixth embodiment of the dilator 600. FIG. 7B is a top view of the portion of the dilator 600 of FIG. 7A; FIG. 7C is a cross-sectional view of the portion of the dilator 600 of FIG. 7B taken through line 7C-7C; and FIG. 7D is a cross-sectional view of the portion of the dilator 600 of FIG. 7C taken through line 7D-7D. In the embodiment of FIGS. 7A-7D, the dilator 600 comprises a plug 614 disposed in a lumen 608 proximal to at least a portion of a port 610. Again, in some embodiments, such as illustrated in FIGS. 3C and 3D, a plug may be configured such that fluid communication is permitted between the proximal end and the distal end of the elongate member. Likewise, in the illustrated embodiment of FIGS. 7C and 7D, the plug 614 does not completely occlude the lumen 608 of an elongate member 602, in contrast to the plug 114 of FIGS. 2A-2D. The illustrated plug 614 comprises a substantially planar surface 620 along a proximal portion of the plug 614. A distal end 616 of the plug 614 defines an angled surface 618 extending from a surface of the lumen opposite of the port 610 to a position at or adjacent a proximal end 611 of the port 610 and substantially in line with an outside surface of the elongate member 602 (FIG. 7D). Thus a substantially L-shaped gap 626, or fluid passage, is formed between the upper surface of the plug 614 and surfaces of both of the lumen 602 and the port 610. As a proximal end of the angled surface 618 of the plug 614 is substantially in line with the outside surface of the elongate member 602, the angled surface 618 may not interfere with threading of a guide wire through the lumen 608 and/or port 610 of the dilator 600. Stated another way, the plug 614 may be configured such that the distal end of the guide wire does not get caught or stuck as it passes into or out of the dilator 600.

As described above for other embodiments of the plug, the plug 614 may be coupled to the elongate member 602. For example, the plug 614 may be bonded or glued to the elongate member 602. In other embodiments, the plug 614 may be integrally formed with the elongate member 602. For example, the plug 614 may be extruded and/or molded as an integral or intrinsic part of the elongate member 602.

Figure 8:
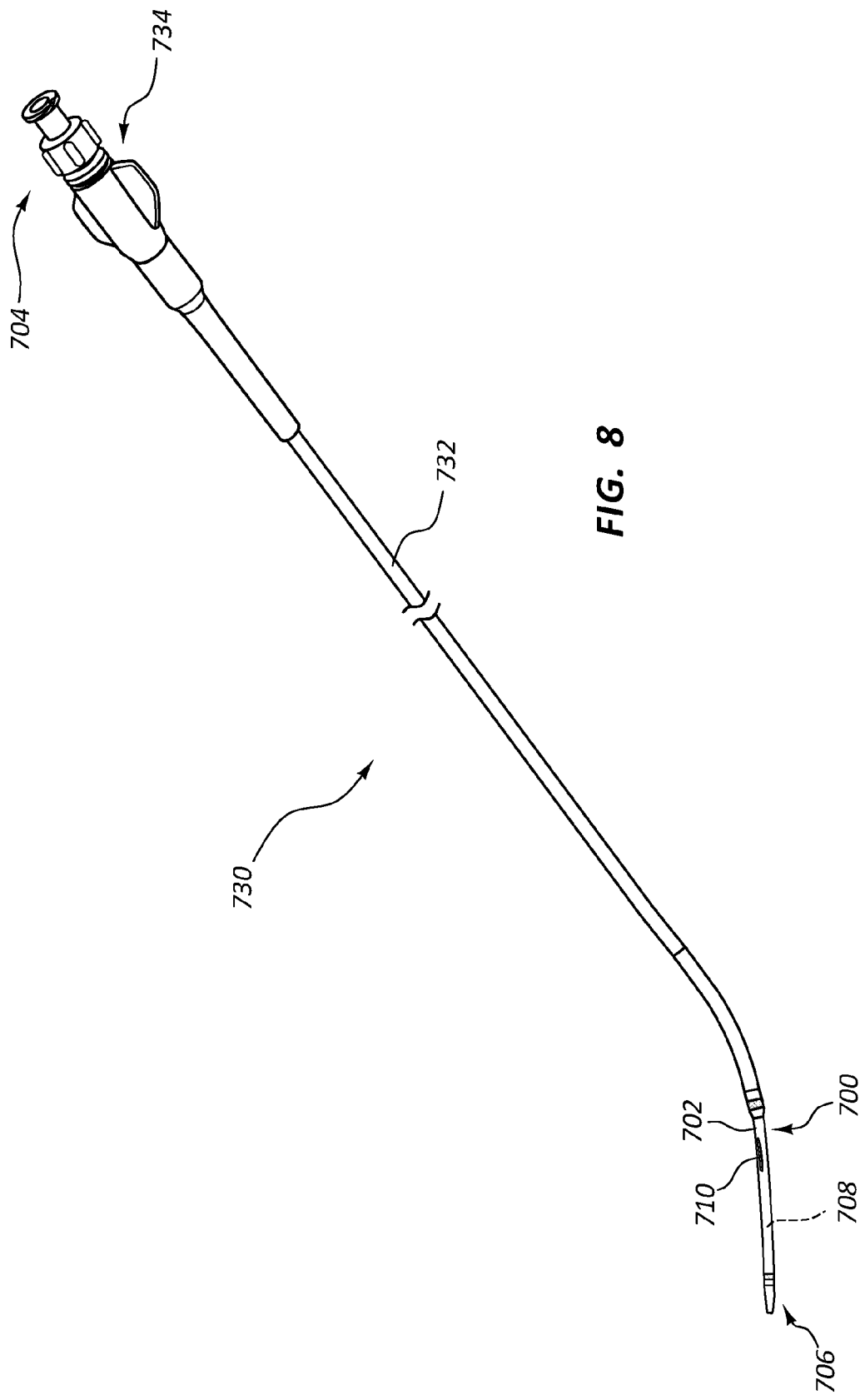
FIG. 8 is a perspective view of an embodiment of a vascular access system.

FIG. 8 is a perspective view of an embodiment of a vascular access system 730. The vascular access system 730 of FIG. 8 may be configured for use during a vascular procedure. Vascular procedures that may be performed using the illustrated vascular access system 730 include, but are not limited to, atherectomy, aspiration, balloon catheterization, diagnostic catheterization, interventional catheterization, snare capture/retrieval, and stent placement/removal. As shown in FIG. 8, the vascular access system 730, may comprise a catheter 732 and a dilator 700 disposed within the catheter 732. The catheter 732 may comprise a sheathless catheter—or a catheter configured for use without an introducer sheath—such as a sheathless guiding catheter or a sheathless guide. Catheters 732 that may be utilized in the vascular access system 730 include, but are not limited to, balloon catheters, diagnostic catheters, guiding catheters, and interventional catheters. In some embodiments, the dilator 700 may be disposable within the catheter 732. In certain embodiments, the dilator 700 may be axially disposable within the catheter 732. In some other embodiments, the dilator 700 may be couplable to the catheter 732. For example, the dilator 700 may be couplable to the catheter 732 at a hub portion 734.

In some embodiments, the dilator 700 may be stiffer, firmer, or more resistant to bending than the catheter 732. Also, in certain embodiments, the dilator 700 may be longer than the catheter 732.

Referring again to the embodiment of FIG. 8, the illustrated dilator 700 comprises an elongate member 702 comprising a proximal end 704 and a distal end 706. The dilator 700 may also comprise a lumen 708 disposed within at least a portion of the elongate member 702. As illustrated, the dilator 700 further comprises a port 710 disposed within a sidewall of the elongate member 702, wherein the port 710 may be in fluid communication with the lumen 708. In some embodiments, the port 710 may be disposed transversely through the sidewall of the elongate member 702. In some other embodiments, the lumen 708 may extend from the proximal end 704 to the distal end 706 of the elongate member 702.

The dilator 700 of the vascular access system 730 may also comprise other elements and/or features of the dilator 100, 200, 300, 400, 500, or 600 described above in connection with FIGS. 1-7D. For example, the dilator 700 may further comprise a plug, similar to plug 114, 214, 314, 414, 514, or 614 illustrated in FIGS. 2A-7D, disposed in the lumen 708 proximal to a portion of the port 710. Furthermore, a distal end of the plug may define an angled surface, similar to angled surface 118 of FIG. 2D, extending from a surface of the lumen opposite of the port 710 to a position at or adjacent to a proximal portion of the port 710.

Similar to the plug 114 illustrated in FIGS. 2A-2D, the plug of the dilator 700 may occlude the lumen 708 such that fluid communication through the lumen 708 between the proximal end 704 and the distal end 706 of the elongate member 702 is blocked, inhibited, or substantially inhibited at the plug. Alternatively, similar to the plugs 214, 314, 414, 514, and 614 illustrated in FIGS. 3A-7D, the plug of the dilator 700 may be configured such that fluid communication is allowed or permitted between the proximal end 704 and the distal end 706 of the elongate member 702 via a gap and/or via a fluid passage. In some embodiments, a fluid passage may comprise a channel or passageway through an inside portion of the plug.

Figure 9:
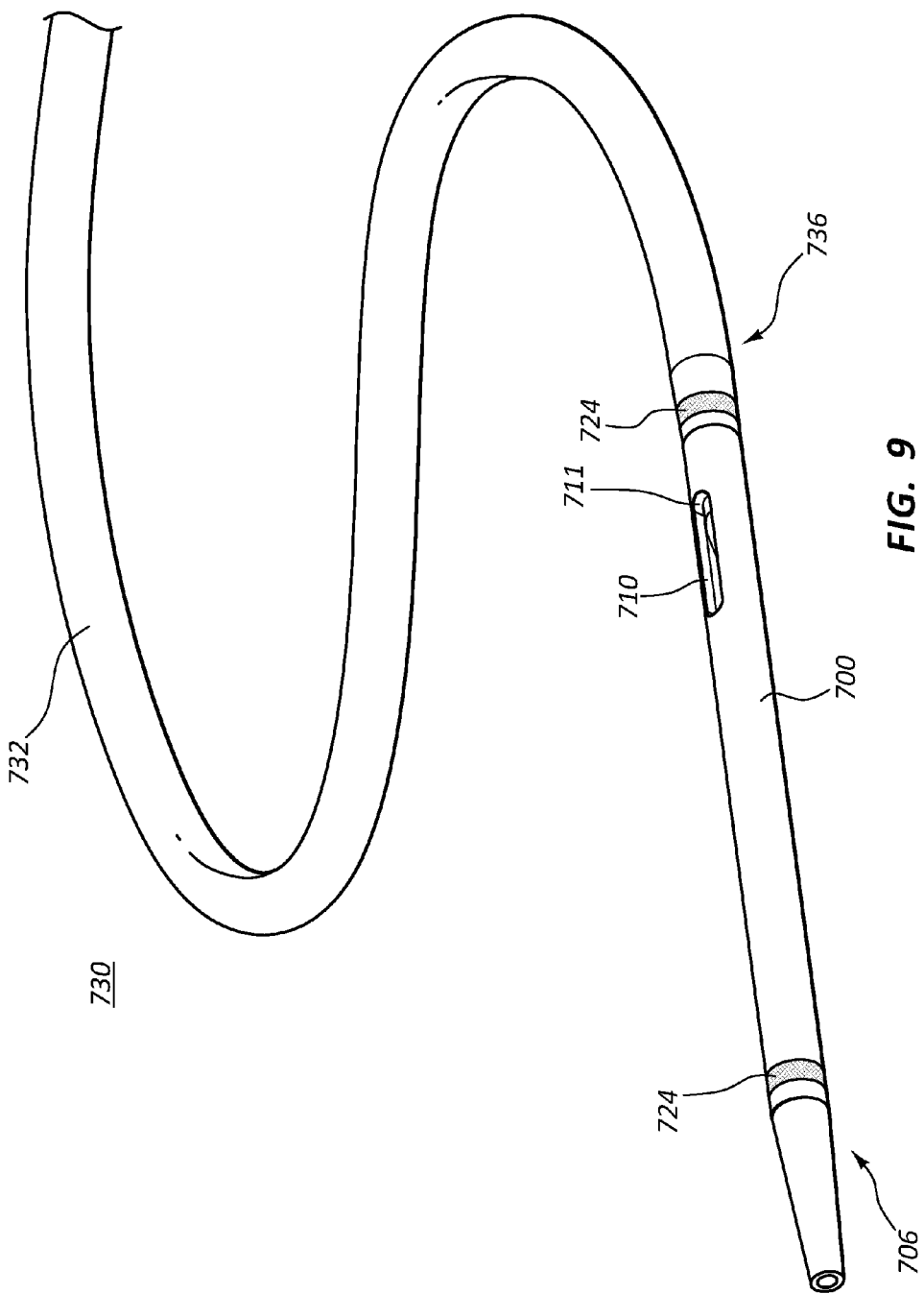
FIG. 9 is a perspective view of a portion of the vascular access system of FIG. 8.

FIG. 9 is a perspective view of a portion of the vascular access system 730 of FIG. 8. In some embodiments, at least a portion of at least one of the catheter 732 and/or the dilator 700 may be radiopaque. For example, the catheter 732 and/or the dilator 700 may comprise one or more radiopaque bands 724. The one or more radiopaque bands 724 may assist a practitioner in determining and/or visualizing the location or position of the vascular access system 730 within a patient. For example, the practitioner may use a fluoroscope, or other imaging device, to visualize the location of the vascular access system 730 within the vasculature of the patient by locating the positions of the one or more radiopaque bands 724. In some embodiments, the radiopaque bands may be positioned at predetermined points along a length of the vascular access system 730. For example, a radiopaque band 724 may be positioned at or adjacent to the distal end 706 of the dilator 700. In another example, a radiopaque band 724 may be positioned at or adjacent to the distal end 736 of the catheter 732.

In some other embodiments, at least a portion of the vascular access system 730 may be hydrophilic or otherwise lubricious. For example, a portion of an outside surface of both of the dilator 700 and the catheter 732 may be hydrophilic such that the outside surface of the vascular access system 730 is lubricious, slippery, and/or smooth such that the vascular access system 730 may be disposed or moved through a percutaneous access site and/or a tortuous and/or narrow vasculature.

In other embodiments, a portion of an outside surface of one or both of the catheter 732 and the dilator 700 of the vascular access system 730 extending from a proximal end 711 of a port 710 may comprise a recess (120' FIG. 2E) configured to accommodate a portion of a guide wire. Such a configuration may aid in disposition or movement of the vascular system in combination with a guide wire through a percutaneous access site and/or through the vasculature.

In some embodiments, the catheter 732 and the dilator 700 may be couplable such that the dilator 700 may be partially disposed within the lumen of the catheter 732. In other embodiments, the catheter 732 and the dilator 700 may be coupled at a hub portion 734 (FIG. 8).

Referring again to FIG. 9, the distal end 706 of the illustrated dilator 700 extends distally relative to a distal end 736 of the catheter 732 when the catheter 732 and the dilator 700 are in a coupled configuration. Also, the illustrated port 710 is disposed distally relative to the distal end 736 of the catheter 732 when the catheter 732 and the dilator 700 are in a coupled configuration. Further, the distal end 736 of the illustrated catheter 732 is tapered such that there is a substantially smooth transition between the distal end 736 of the catheter 732 and the dilator 700. In other embodiments, the distal end 706 of the illustrated dilator 700 is tapered. In certain embodiments, a tapered portion of the dilator 700 may be longer than a tapered portion of the catheter 732. Other configurations of the catheter 732 and the dilator 700, such as catheters and dilators lacking tapered ends, are also within the scope of this disclosure.

Figure 10A:
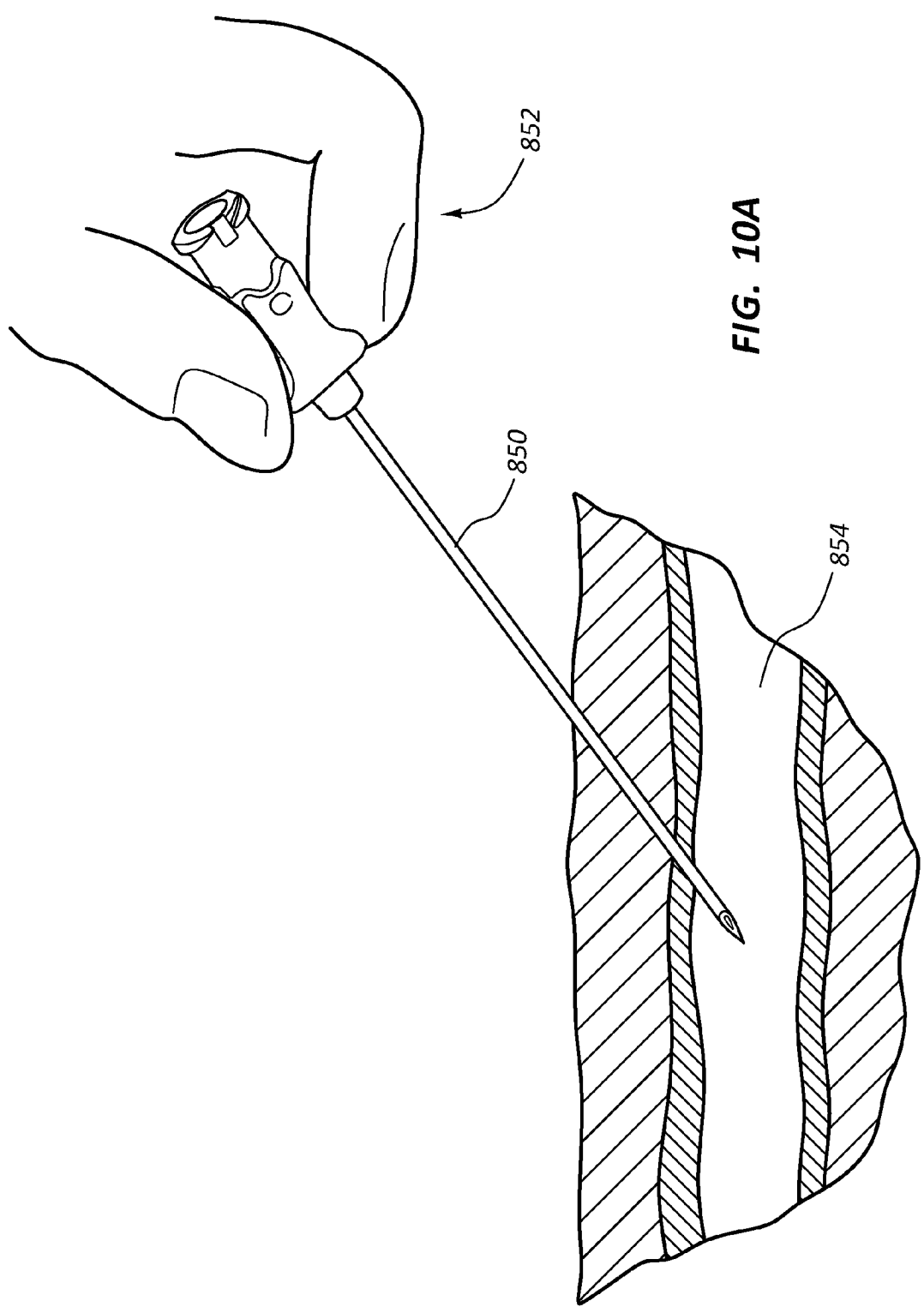
FIG. 10A is a view showing introduction of a needle into a vessel.

Methods of accessing a percutaneous site of a patient are also disclosed. The methods may facilitate completion of a procedure in fewer steps such that less equipment and/or fewer components may be utilized. In some instances, conducting fewer steps and/or utilizing fewer components may result in smaller access sites such that the methods may result in a lower incidence of arterial spasm and improved and/or quicker patient healing. In certain embodiments, methods of accessing a percutaneous access site may comprise introduction of a needle 850 into a vessel 854 of a patient. FIG. 10A is a view showing introduction of the needle 850 into the vessel 854. In some embodiments, a practitioner 852 may introduce the needle 850 into the vessel 854 of a patient. In other embodiments, the vessel 854 may include, but is not limited to, the radial artery, the brachial artery, or the femoral artery. For example, the dilators and/or vascular access systems of the present disclosure may be adapted for use in accessing the femoral artery, in contrast to accessing the radial artery, by the use of a larger needle, dilator, catheter, guide wire, and/or other components.

Figure 10B:
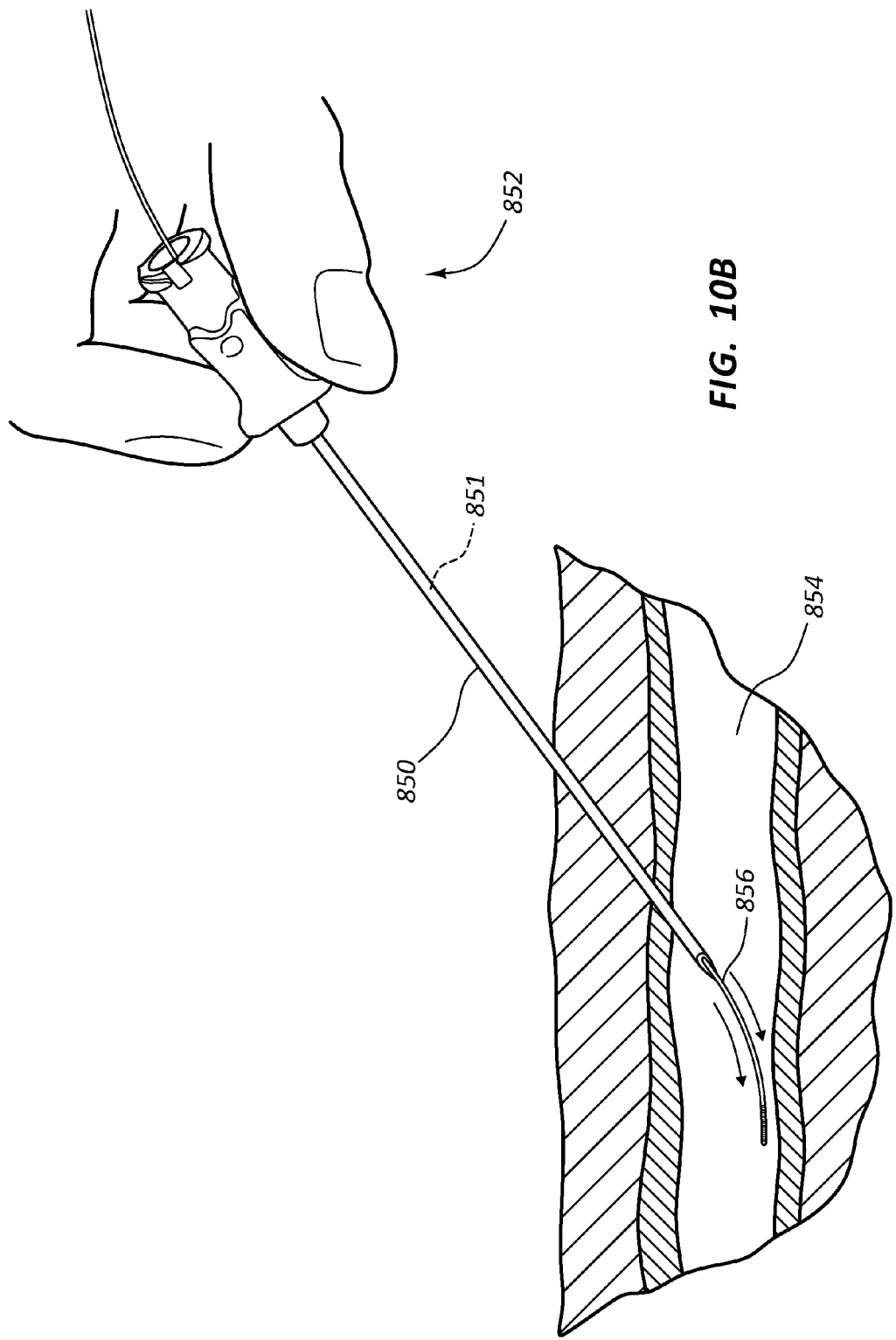
FIG. 10B is a view showing introduction of a first guide wire into the vessel through a lumen of the needle.

In some embodiments, the methods may further comprise introducing a first guide wire 856 into the vessel 854 via the introduced needle 850. FIG. 10B is a view showing introduction of the first guide wire 856 into the vessel 854 through a lumen 851 of the needle 850. In certain embodiments, the practitioner 852 may introduce the first guide wire 856 into the vessel 854 through the lumen 851 of the needle 850. In other embodiments, the practitioner 852 may introduce more than one guide wire into the vessel 854, for example, two guide wires, three guide wires, and so on. The arrows, as shown in FIG. 10B, illustrate the introduction of the first guide wire 856 into the vessel 854 via the needle 850. Different sizes of guide wires may be used in the disclosed method. In some embodiments, a 0.018 inch diameter guide wire 856 may be used. In other embodiments, 0.021 inch, 0.025 inch, 0.032 inch, 0.035 inch, or 0.038 inch diameter guide wires 856 may be used. In some other embodiments, guide wires 856 of other diameters may be used.

Figure 10C:
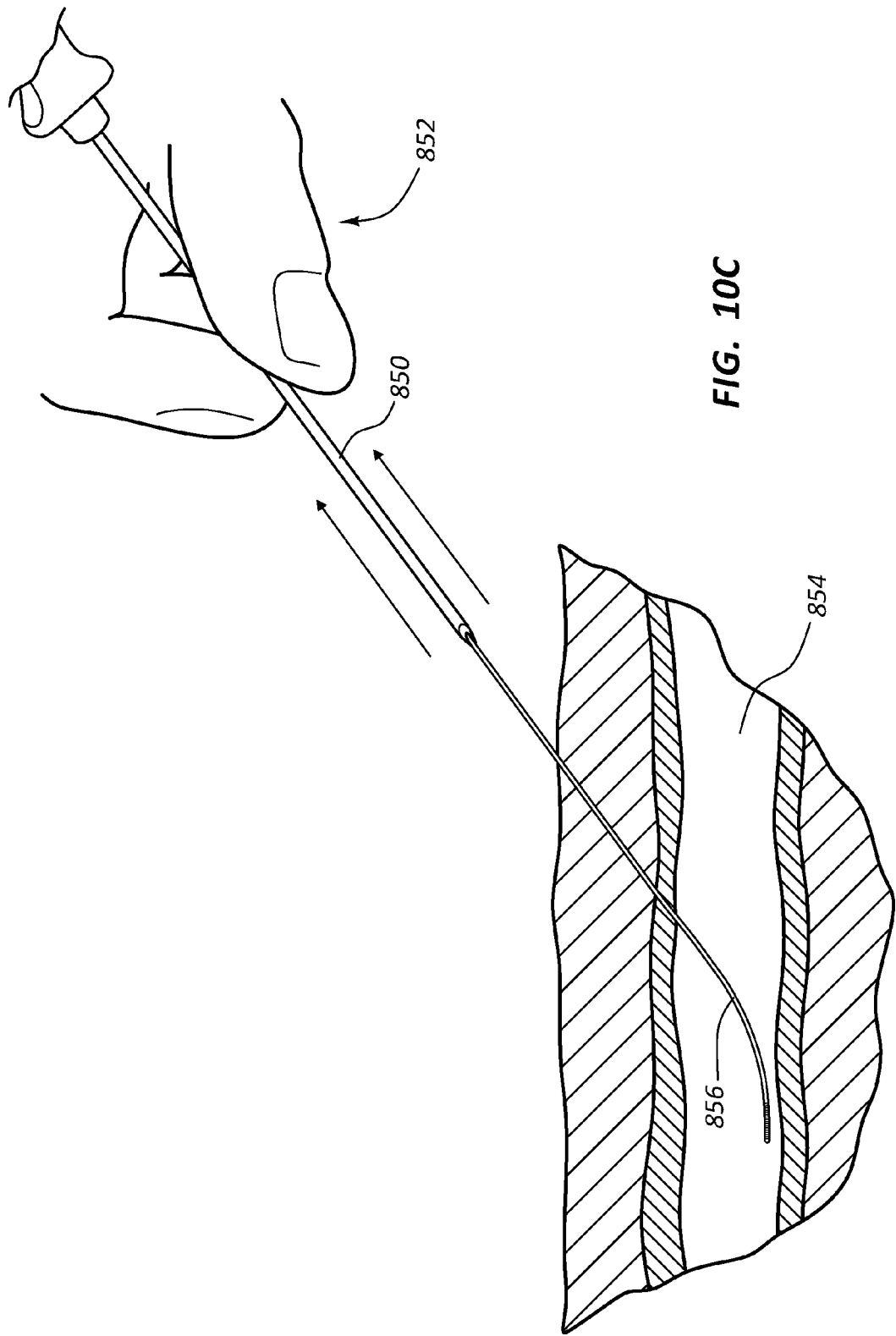
FIG. 10C is a view showing removal of the needle from the vessel.

The methods may also further comprise extraction of the needle 850 from the vessel 854. FIG. 10C is a view showing removal of the needle 850 from the vessel 854. In some embodiments, the practitioner 852 may remove the needle 850 from the vessel 854 while leaving the first guide wire 856 disposed within the vessel 854. The arrows, as shown in FIG. 10C, illustrate the removal of the needle 850 from the vessel 854.

Figure 10D:
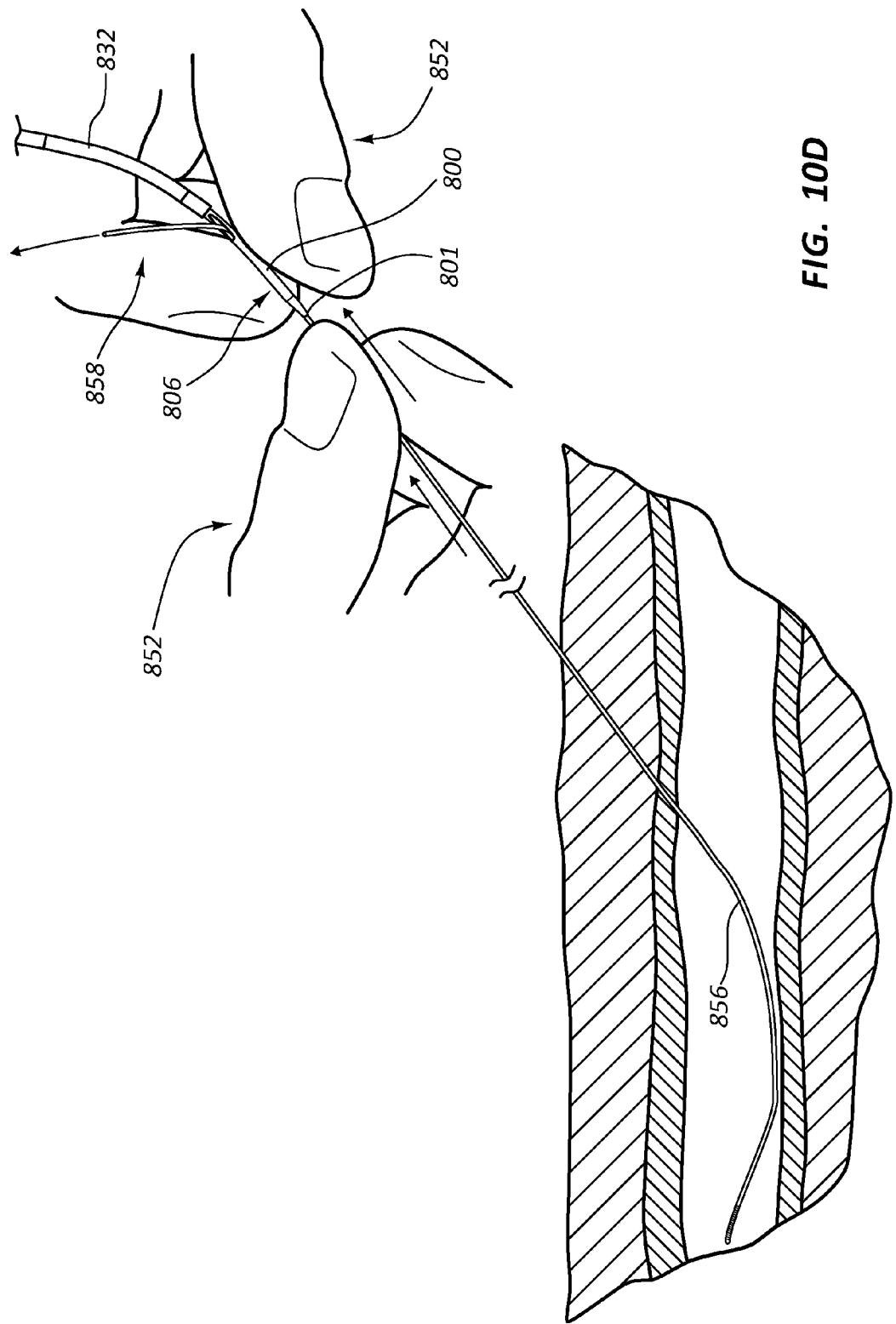
FIG. 10D is a view showing threading of a proximal end of the first guide wire through a distal end of a dilator wherein the dilator is disposed within a catheter.

In some embodiments, the methods may further comprise introduction of the first guide wire 856 into a dilator 800. FIG. 10D is a view showing threading of the first guide wire 856 through an opening 801 at a distal end 806 of the dilator 800, wherein the dilator 800 is disposed within a catheter 832. In certain embodiments, the practitioner 852 may insert a proximal end 858 of the first guide wire 856 through the opening 801 at or adjacent to the distal end 806 of the dilator 800, as indicated by the arrows. As illustrated, a portion of the dilator 800 is disposed within the catheter 832. In certain embodiments, a portion of the dilator 800 may be axially disposed within the catheter 832. In other embodiments, the dilator 800 may not be disposed within a catheter 832. In some embodiments, the size of the catheter 832 may be 5 F (French size). In some other embodiments, the catheter 832 may be 6 F, 7 F, or 8 F. Other sizes of catheters 832 are also contemplated.

Figure 10E:
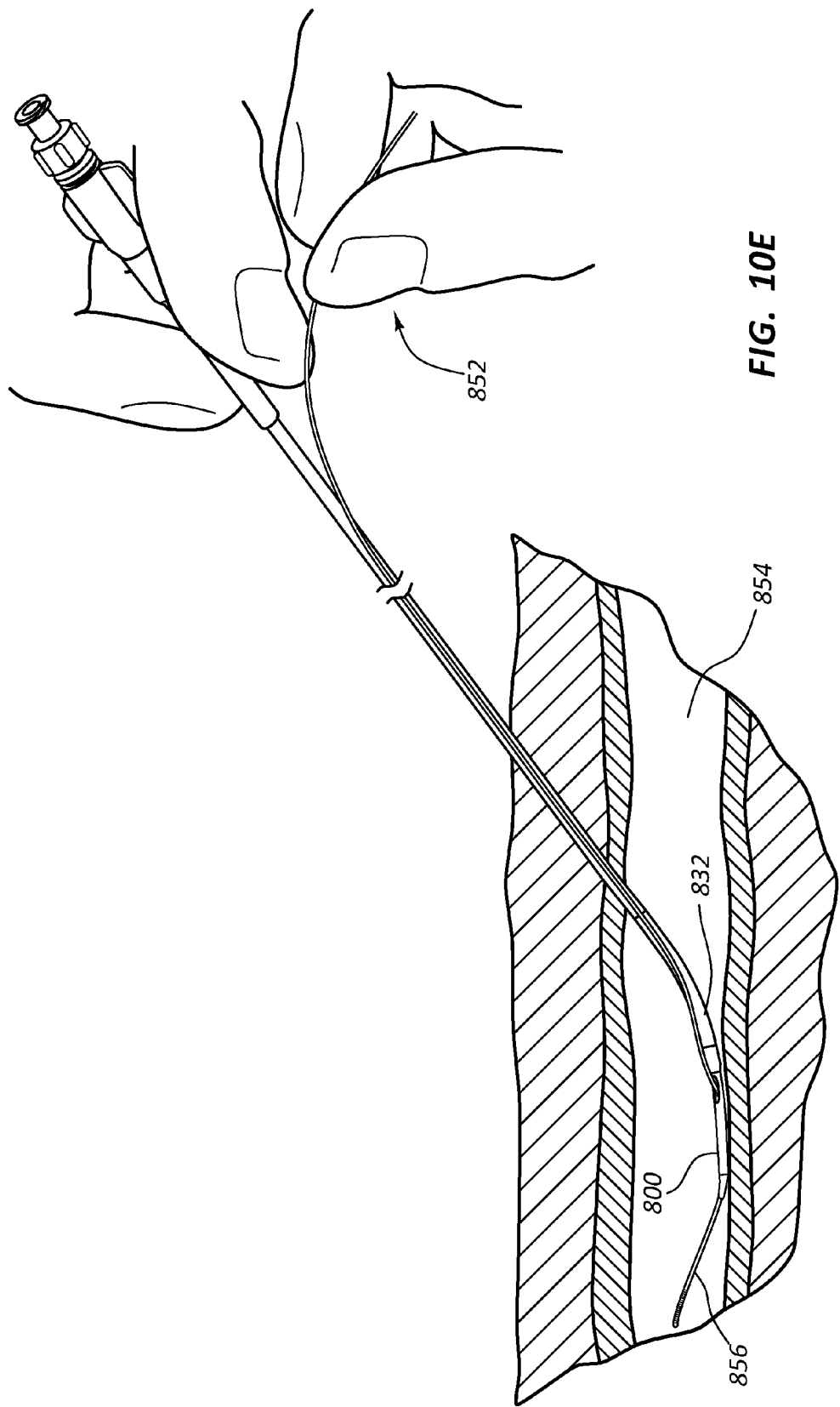
FIG. 10E is a view showing disposition of the dilator and the catheter in the vessel.

The methods may further comprise introducing the dilator 800 and/or the catheter 832 into the vessel 854. FIG. 10E is a view showing disposition of the dilator 800 and the catheter 832 into the vessel 854. In some embodiments, the practitioner 852 may introduce both of the dilator 800 and the catheter 832 into the vessel 854 of the patient along at least a portion of the first guide wire 856. In other embodiments, the practitioner may flush the dilator 800 and/or catheter 832 with saline solution, heparinized saline solution, water, and/or another physiologically compatible sterile fluid prior to introduction of the dilator 800 and/or catheter into the vessel 854 of the patient.

Figure 10F:
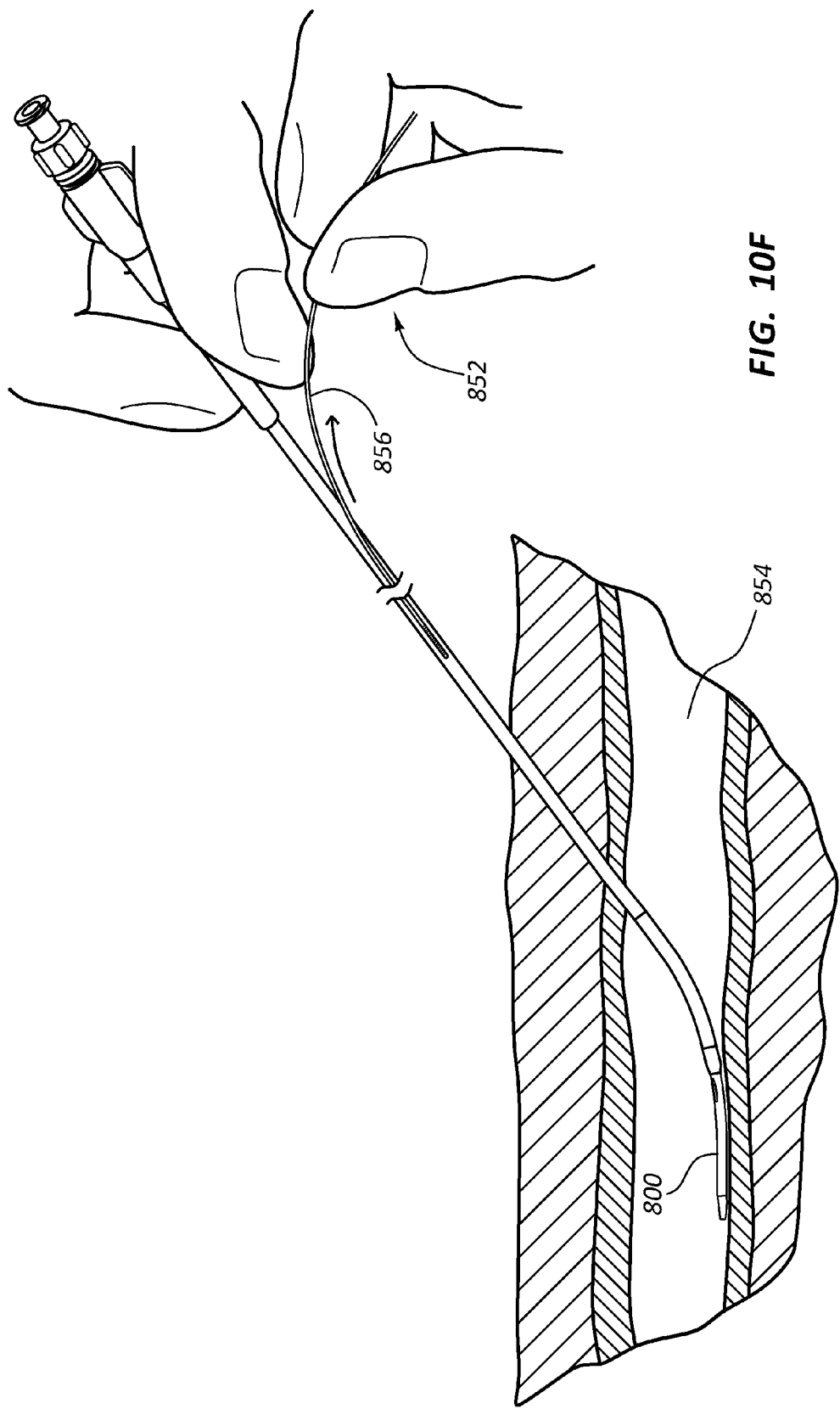
FIG. 10F is a view showing removal of the first guide wire from the vessel.
Figure 10G:
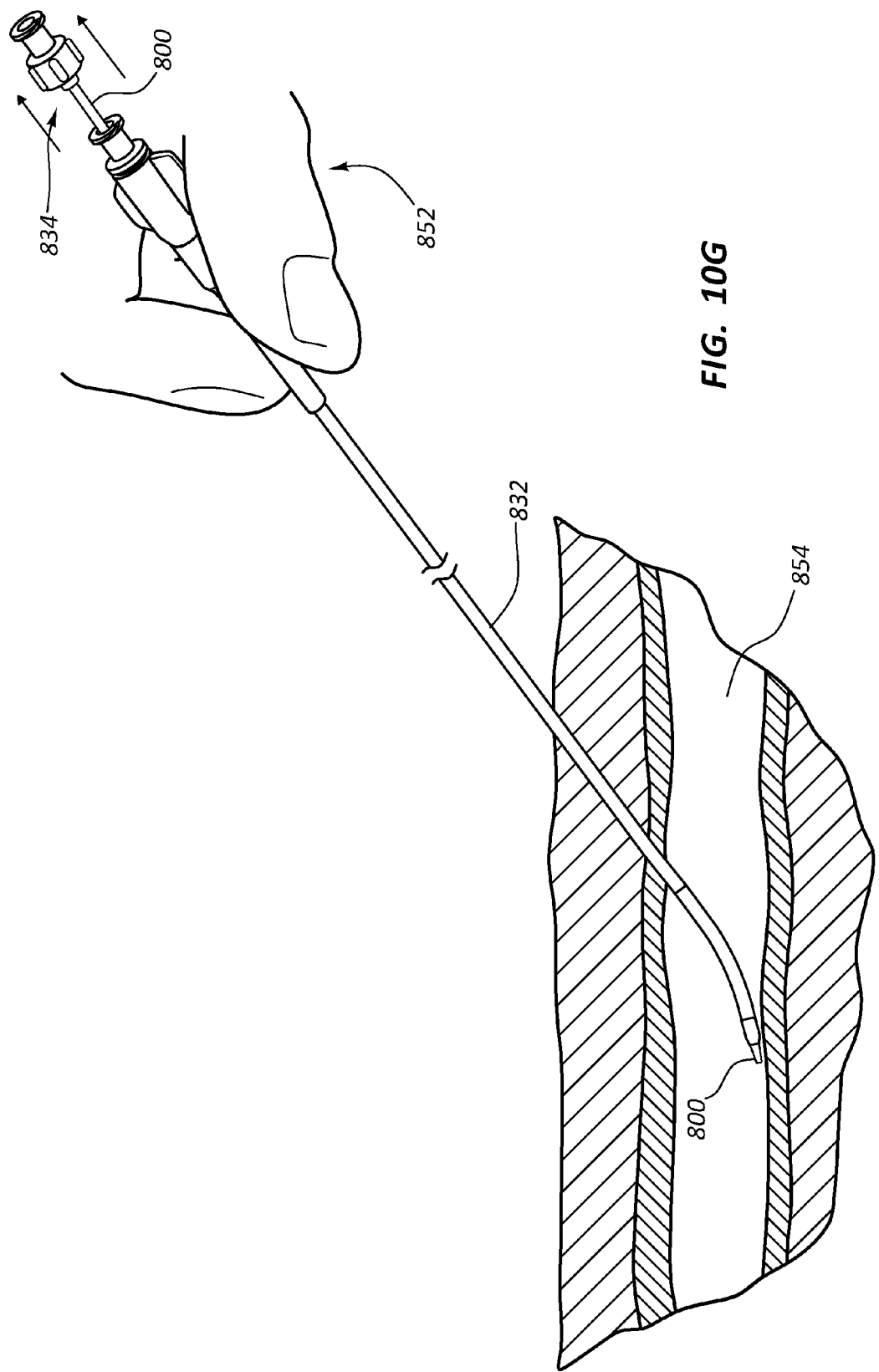
FIG. 10G is a view showing removal of the dilator from the vessel.

In certain embodiments, the methods may further comprise extracting the first guide wire 856 and/or the dilator 800 from the vessel 854. FIG. 10F is a view showing removal of the first guide wire 856 from the vessel 854. In some embodiments, the practitioner 852 may remove the first guide wire 856 from both of the dilator 800 and the vessel 854. FIG. 10G is a view showing removal of the dilator 800 from the vessel 854. In other embodiments, the practitioner 852 may remove the dilator 800 from both of the vessel 854 and the catheter 832, as indicated by the arrows. The dilator 800 may be decoupled from the catheter 832 at a hub portion 834. In some other embodiments, the dilator 800 may not be coupled to the catheter 832 at a hub portion 834.

Figure 10H:
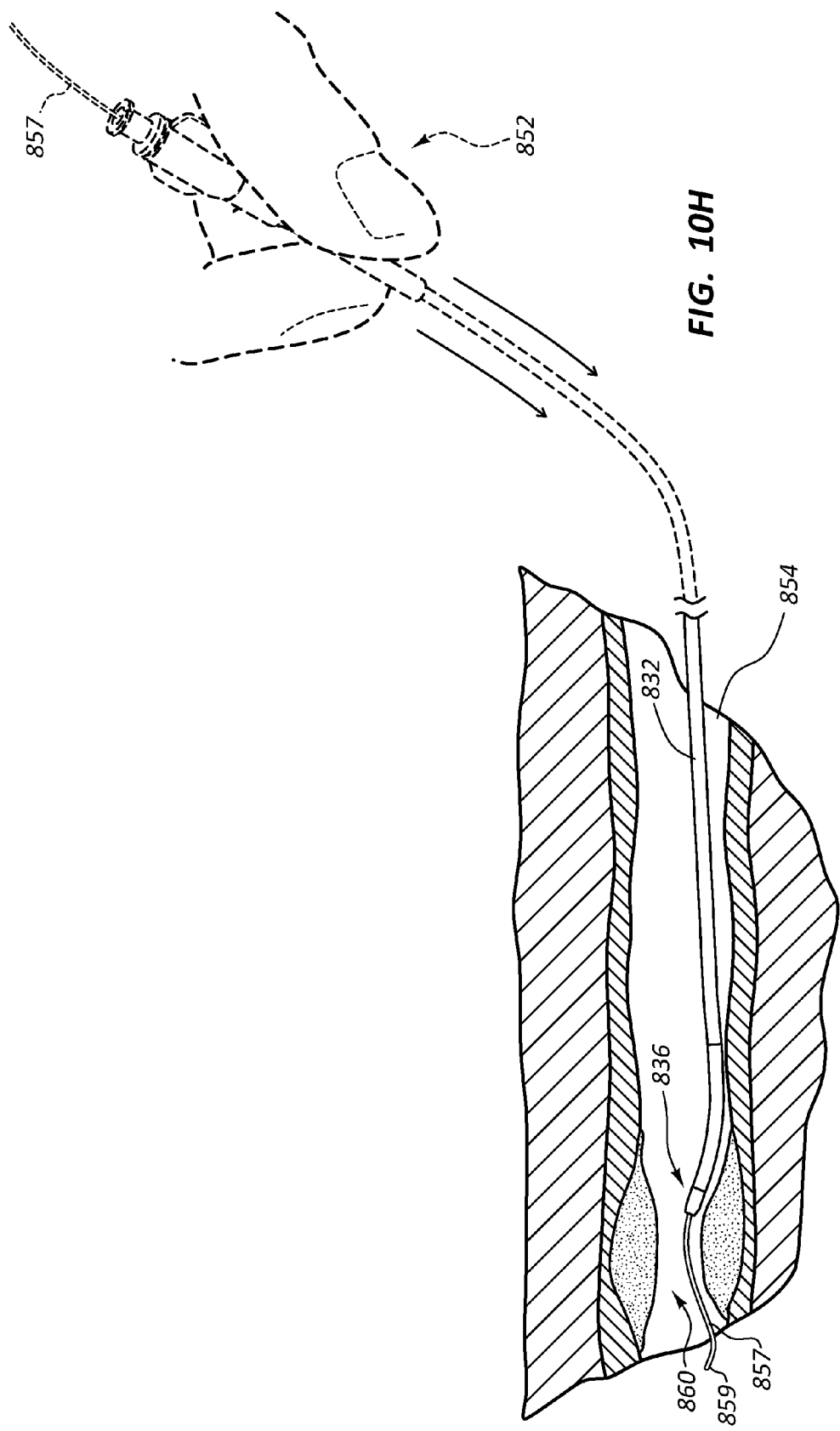
FIG. 10H is a view showing disposition of a second guide wire through the catheter.

In some embodiments, the methods may comprise introduction of a second guide wire 857 through the catheter 832. FIG. 10H is a view showing introduction of the second guide wire 857 into or through the catheter 832. The practitioner 852 may displace a distal end 859 of the second guide wire 857 through the vessel 854 to a position at or adjacent a therapy site 860. The catheter 832 may then be advanced or threaded along the second guide wire 857 such that a distal end 836 of the catheter 832 is disposed at or adjacent the therapy site 860.

Figure 10I:
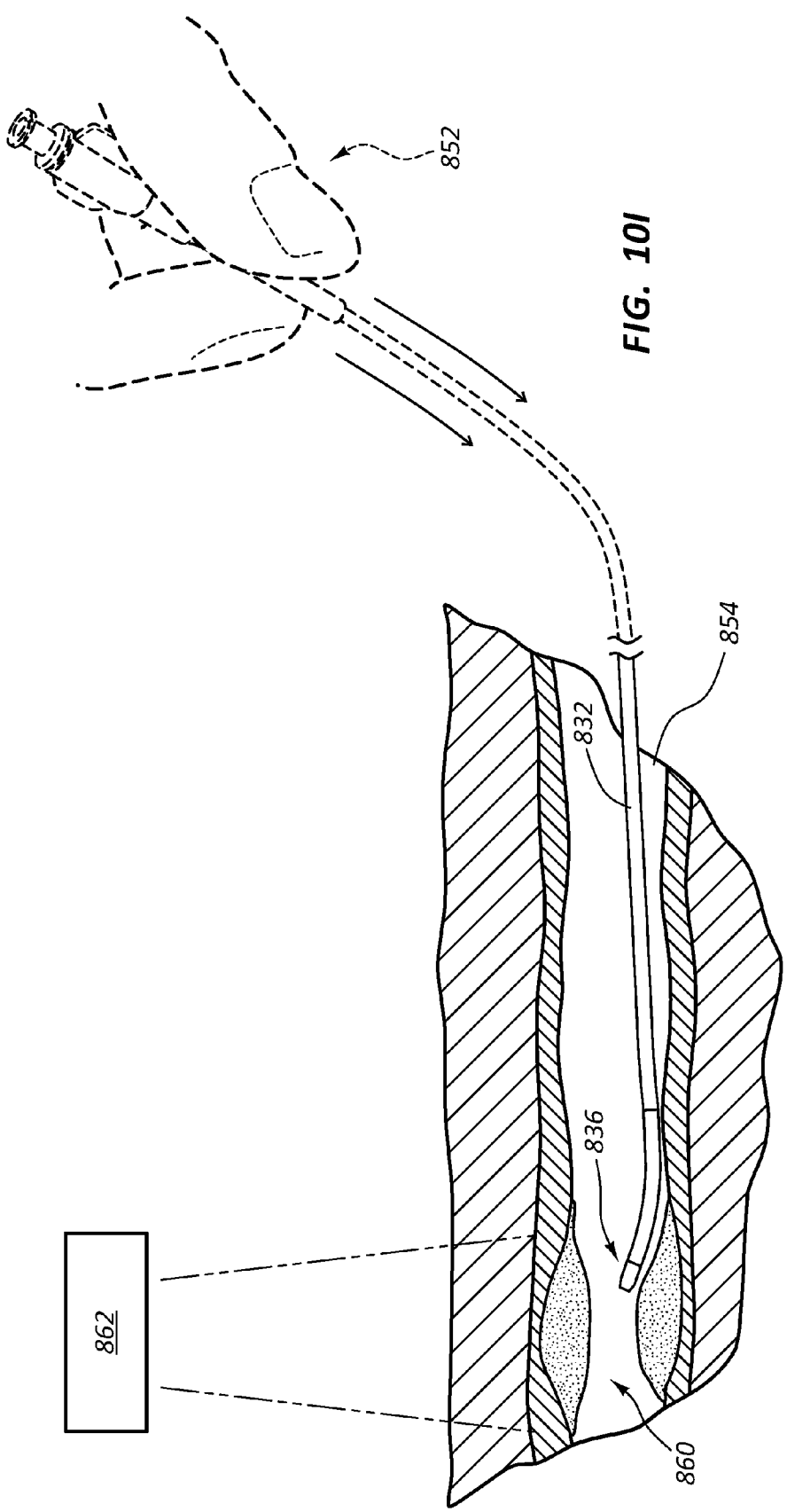
FIG. 10I is a view showing disposition and visualization of the disposition of a distal end of the catheter at a therapy site.

The methods may further comprise placement of the catheter 832 at a therapy site 860 without threading or displacing the catheter 832 along a guide wire, such as the second guide wire 857 illustrated in FIG. 10H. FIG. 10I is a view showing disposition and visualization of the disposition of a distal end 836 of the catheter 832 at a therapy site 860. The therapy site 860 may be the site, for example, of an embolus, an occlusion, a plaque, or another feature. In some embodiments, the practitioner 852 may displace the catheter 832 through the vessel 854 such that a distal end 836 of the catheter 832 is disposed at or adjacent to the therapy site 860 within the patient. An imaging device 862, such as a fluoroscope, may be used to visualize the placement or positioning of the distal end 836 of the catheter 832.

In certain embodiments, the methods may further comprise conducting a vascular procedure. FIG. 10J is a view showing performance and visualization of the performance of a vascular procedure at the therapy site 860. In some embodiments, the practitioner 852 may displace a medical device 864 through a lumen of the catheter 832 such that the medical device 864 is disposed at or adjacent to the therapy site 860 within the vessel 854 of the patient. The practitioner 852 may then perform a vascular procedure at or adjacent to the therapy site 860 within the vessel 854 of the patient. An imaging device 862, such as a fluoroscope, may be used to visualize the performance of the vascular procedure at the therapy site 860. The medical device 864 may include, but is not limited to, an atherectomy device, an aspirator, a balloon catheter (as illustrated in FIG. 10J), a diagnostic catheter, a guiding catheter, an interventional catheter, a snare, or a stent.

In other embodiments, the methods may further comprise extraction of the catheter 832 from the patient. FIG. 10K is a view showing removal of the catheter 832 from the vessel 854. In some embodiments, the practitioner 852 may remove the medical device 864 and/or the catheter 832 from the vessel 854 of the patient as indicated by the dashed arrows.

EXEMPLARY EMBODIMENTS

The following embodiments are illustrative and exemplary and not meant as a limitation of the scope of the present disclosure in any way.

I. Dilators for Percutaneous Access

In one embodiment, a dilator configured for percutaneous access comprises: (1) an elongate member comprising a proximal end and a distal end; (2) a lumen disposed within at least a portion of the elongate member; and (3) a port disposed in a sidewall of the elongate member, wherein the port is in fluid communication with the lumen.

The lumen may extend from the proximal end to the distal end of the elongate member.

The dilator may further comprise a plug disposed in the lumen proximal to a portion of the port.

A distal end of the plug may define an angled surface extending from a surface of the lumen opposite of the port to a position at or adjacent a proximal portion of the port.

The angled surface may be configured to direct a guide wire extending from the distal end of the elongate member through the port.

The plug may occlude the lumen such that fluid communication through the lumen between the proximal end and the distal end of the elongate member is inhibited at the plug.

The plug may be configured such that fluid communication is permitted between the proximal end and the distal end of the elongate member.

The plug may comprise a fluid passage.

The plug may comprise a check valve.

The plug may be coupled to the elongate member.

The lumen may extend from the distal end of the elongate member to the port.

The lumen may be configured to direct a guide wire extending from the distal end of the elongate member through the port.

A portion of the elongate member may be radiopaque.

A portion of the distal end of the elongate member may be tapered.

A portion of the elongate member may be hydrophilic.

A portion of an outside surface of the elongate member extending from a proximal end of the port may comprise a recess configured to accommodate a portion of a guide wire.

II. Apparatuses for Percutaneous Access

In one embodiment, an apparatus configured for a percutaneous access site, comprises: an elongate member configured for passage of fluid through at least a portion of the elongate member; wherein the elongate member is configured for passage of a guide wire through only a portion of the elongate member; and wherein the guide wire is displaceable along a portion of the elongate member through a first opening of the elongate member and wherein the elongate member comprises an angled guiding surface configured to direct the guide wire out a second opening of the elongate member.

The elongate member may be configured for passage of fluid along substantially an entire length of the elongate member.

The second opening may be disposed in a sidewall of the elongate member.

III. Vascular Access Systems

In one embodiment, a vascular access system configured for use during a vascular procedure comprises: (1) a catheter; and (2) a dilator disposable within the catheter, wherein the dilator comprises: (a) an elongate member comprising a proximal end and a distal end, (b) a lumen disposed within at least a portion of the elongate member, and (c) a port disposed in a sidewall of the elongate member, wherein the port is in fluid communication with the lumen.

The lumen may extend from the proximal end to the distal end of the elongate member.

The dilator may further comprise a plug disposed in the lumen proximal to a portion of the port.

A distal end of the plug may define an angled surface extending from a surface of the lumen opposite of the port to a position at or adjacent a proximal portion of the port.

The plug may occlude the lumen such that fluid communication through the lumen between the proximal end and the distal end of the elongate member is inhibited at the plug.

The plug may be configured such that fluid communication is permitted between the proximal end and the distal end of the elongate member.

The plug may comprise a fluid passage.

The system may be configured such that a guide wire cannot pass through the fluid passage.

A portion of at least one of the catheter or the dilator may be radiopaque.

A portion of one or both of the catheter and the dilator may be hydrophilic.

A portion of an outside surface of one or both of the catheter and the dilator extending from a proximal end of the port may comprise a recess configured to accommodate a portion of a guide wire.

The catheter and the dilator may be couplable such that the dilator is partially disposed within a lumen of the catheter.

A distal end of the dilator may extend distally relative to a distal end of the catheter when the catheter and the dilator are coupled.

The port may be disposed distally relative to the distal end of the catheter when the dilator and the catheter are coupled.

The distal end of the catheter may be tapered such that there is a smooth transition between the distal end of the catheter and the dilator, and wherein the distal end of the dilator is tapered.

A tapered portion of the dilator may be longer than a tapered portion of the catheter.

The dilator may be stiffer than the catheter.

The dilator may be longer than the catheter.

IV. Method of Accessing Percutaneous Sites

In one embodiment, a method of accessing a percutaneous site of a patient, comprises: (1) inserting a proximal end of a first guide wire through an opening at or adjacent a distal end of a dilator, wherein a portion of the dilator is disposed within a catheter; (2) threading the first guide wire through both of a portion of a lumen of the dilator and a port disposed in a sidewall of the dilator; and (3) introducing both the dilator and the catheter into a vessel of the patient along a portion of the first guide wire.

The method may further comprise: (1) introducing a needle into the vessel; (2) introducing the first guide wire into the vessel through a lumen of the needle; and (3) removing the needle from the vessel prior to inserting the proximal end of the first guide wire through the opening at or adjacent the distal end of the dilator.

The method may further comprise: (1) removing the first guide wire and the dilator from the vessel; and (2) displacing the catheter through the vessel such that a distal end of the catheter is disposed at or adjacent a therapy site within the patient subsequent to introducing both the dilator and the catheter into the vessel along a portion of the first guide wire.

The method may further comprise: (1) removing the first guide wire and the dilator from the vessel; (2) introducing a second guide wire through the catheter; (3) disposing a distal end of the second guide wire at or adjacent a therapy site; and (4) advancing the catheter along the second guide wire such that a distal end of the catheter is disposed at or adjacent the therapy site.

The method may further comprise displacing a medical device through the catheter such that the medical device is disposed at or adjacent a therapy site within the vessel.

The method may further comprise performing a vascular procedure at or adjacent the therapy site within the vessel.

The medical device may be selected from at least one of: an atherectomy device, an aspirator, a balloon catheter, a diagnostic catheter, a guiding catheter, an interventional catheter, a snare, or a stent.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. It is intended that the scope of the invention be defined by the claims appended hereto and their equivalents.

The invention claimed is:

1. A dilator configured for percutaneous access, the dilator comprising:
    an elongate member comprising a proximal end and a distal end;
    a lumen disposed within at least a portion of the elongate member;
    a port disposed in a sidewall of the elongate member, wherein the port is in fluid communication with the lumen; and
    a plug disposed in the lumen proximal to a portion of the port, wherein the plug is fixedly coupled to the elongate member,
    wherein a distal end of the plug defines an angled surface permanently attached to and extending from a surface of the lumen opposite of the port to a position at or adjacent a proximal portion of the port, and
    wherein the plug comprises a fluid passage and the plug is configured for the passage of fluid from the proximal end to the distal end of the elongate member.

2. The dilator of claim 1, wherein the lumen extends from the proximal end to the distal end of the elongate member.

3. The dilator of claim 1, wherein the angled surface is configured to direct a guide wire extending from the distal end of the elongate member through the port.

4. The dilator of claim 1, wherein the lumen extends from the distal end of the elongate member to the port.

5. The dilator of claim 4, wherein the lumen is configured to direct a guide wire extending from the distal end of the elongate member through the port.

6. The dilator of claim 1, wherein a portion of the elongate member is hydrophilic.

7. The dilator of claim 1, wherein a portion of an outside surface of the elongate member extending from a proximal end of the port comprises a recess disposed on the outside surface configured to accommodate a portion of a guide wire, and aid in disposition of the dilator in combination with the guide wire through a patient's percutaneous access site and/or vasculature.

8. The dilator of claim 1, wherein the fluid passage is configured to inhibit passage of a guide wire.

9. The dilator of claim 1, wherein a portion of the angled surface extends at least partially through the port.

10. An apparatus configured for a percutaneous access site, comprising:
    an elongate member configured for passage of fluid through a lumen of the elongate member;
    wherein the elongate member is configured for passage of a guide wire through only a portion of the elongate member;
    wherein the guide wire is displaceable along the portion of the elongate member through a first opening of the elongate member;
    wherein the elongate member comprises an angled guiding surface configured to direct the guide wire out of a second opening of the elongate member, the angled guiding surface permanently attached to and extending from a surface of the lumen opposite of the second opening of the elongate member to a position at or adjacent a proximal portion of the second opening and wherein the angled guiding surface comprises a fluid passage configured for the passage of fluid through the lumen of the elongate member; and
    wherein a portion of an outside surface of the elongate member extending from a proximal end of the second opening comprises a recess disposed on the outside surface configured to accommodate a portion of the guide wire, and aid in disposition of the apparatus in combination with the guide wire through a patient's percutaneous access site and/or vasculature.

11. The apparatus of claim 10, wherein the elongate member is configured for passage of fluid along substantially an entire length of the elongate member.

12. The apparatus of claim 10, wherein the second opening is disposed in a sidewall of the elongate member.

13. A method of accessing a percutaneous site of a patient, comprising:

inserting a proximal end of a first guide wire through an opening at or adjacent a distal end of a dilator, wherein a portion of the dilator is disposed within a catheter;

threading the first guide wire through both of a portion of a lumen of the dilator and a port disposed in a sidewall of the dilator, wherein threading the first guide wire comprises advancing the first guide wire to a plug disposed in the lumen, wherein the plug defines an angled surface permanently attached to and extending from a surface of the lumen opposite the port to a position at or adjacent a proximal portion of the port and wherein the plug comprises a fluid passage configured for the passage of fluid through the lumen of the dilator; and introducing both the dilator and the catheter into a vessel of the patient along a portion of the first guide wire.

14. The method of claim 13, further comprising:
removing the first guide wire and the dilator from the vessel; and
displacing the catheter through the vessel such that a distal end of the catheter is disposed at or adjacent a therapy site within the patient subsequent to introducing both the dilator and the catheter into the vessel along the portion of the first guide wire.

15. The method of claim 13, further comprising:
displacing a medical device through the catheter such that the medical device is disposed at or adjacent a therapy site within the vessel.

16. The method of claim 15, wherein the medical device is selected from at least one of: an atherectomy device, an aspirator, a balloon catheter, a diagnostic catheter, a guiding catheter, an interventional catheter, a snare, or a stent.

* * * * *